(12) United States Patent
Mach et al.

(10) Patent No.: US 9,035,057 B2
(45) Date of Patent: May 19, 2015

(54) DIHYDROETHIDINE ANALOGUES AND USES THEREOF

(75) Inventors: Robert H. Mach, Eureka, MO (US);
Mark Mintun, Villanova, PA (US);
Wenhua Chu, Saint Louis, MO (US);
Laura Dugan, San Diego, CA (US)

(73) Assignee: Washington University, Saint Louis, MO (US)

( * ) Notice: Subject to any disclaimer, the term of this patent is extended or adjusted under 35 U.S.C. 154(b) by 199 days.

(21) Appl. No.: 13/516,783

(22) PCT Filed: Dec. 16, 2010

(86) PCT No.: PCT/US2010/060735
§ 371 (c)(1),
(2), (4) Date: Jun. 18, 2012

(87) PCT Pub. No.: WO2011/084585
PCT Pub. Date: Jul. 14, 2011

(65) Prior Publication Data
US 2013/0079522 A1     Mar. 28, 2013

Related U.S. Application Data

(60) Provisional application No. 61/287,115, filed on Dec. 16, 2009.

(51) Int. Cl.
*C07D 401/12*     (2006.01)
*C07D 221/12*     (2006.01)

(52) U.S. Cl.
CPC ............ *C07D 221/12* (2013.01); *C07D 401/12* (2013.01)

(58) Field of Classification Search
CPC ............................ C07D 221/12; C07D 401/12
USPC ......................................................... 546/109
See application file for complete search history.

(56) References Cited

PUBLICATIONS

Electrophoresis. Abstract, Oct. 1996;17(10):1524-7. The effect of ethidium bromide on mobility of DNA fragments in agarose gel electrophoresis. Sigmon J1.*
Commonly Used Techniques in Appendix 3Biochemistry and Molecularbiology by Daniel Voytas, 1999.*
Behrens, M.M., et al., "Ketamine-induced loss of phenotype of fast-spiking interneurons is mediated by NADPH-oxidase." Science. 318:1645-1647, 2007.
Garbett, N. C., et al., "Influence of the amino substituents in the interaction of ethidium bromide with DNA." Biophys. J. 87: 3974-3981, 2004.
Panagiotidis, G., et al., "Influence of nitric oxide synthase inhibition, nitric oxide and hydroperoxide on insulin release induced by various secretagogues." Br. J. Pharmacol. 114: 289-296, 1995.
Quick, K.L. and Dugan, L.L., "Superoxide stress identifies neurons at risk in a model of ataxia-telangiectasia." Ann. Neurology, 49:627-635, 2001.

\* cited by examiner

*Primary Examiner* — Rita Desai
(74) *Attorney, Agent, or Firm* — Saul L. Zackson; Zackson Law LLC

(57) ABSTRACT

Tracers for imaging distribution of reactive oxygen species (ROS) are disclosed. The tracers include radiolabeled dihydroethidine (DHE) analogues. Further disclosed are uses of the compounds, including methods of imaging tissue distribution of ROS in vivo by positron emission tomography (PET). Methods of synthesizing the compounds are also disclosed.

16 Claims, 11 Drawing Sheets

COLOR IMAGE

BRAIN

| NO DHE | DHE | WC-63 | WC-77 | WC-81 |

CHEST

BLUE CHANNEL

DIHYDROETHIDINE ANALOGUES AND USES THEREOF

STATEMENT REGARDING FEDERALLY SPONSORED RESEARCH OR DEVELOPMENT

The disclosed subject matter was developed in part with Government support under grant RC1AG036045 from the National Institutes of Health. The Government has certain rights in the invention.

CROSS-REFERENCE TO RELATED APPLICATIONS

This application claims the benefit of and the priority to PCT application PCT/U.S. Ser. No. 10/060,735 filed on Dec. 16, 2010 and U.S. Provisional Application Ser. No. 61/287,115 filed on Dec. 16, 2009, each of which is incorporated herein by reference in its entirety.

INTRODUCTION

The present teachings relate to the field of free radicals in biology and medicine.

Free radicals play key roles in the pathogenesis of a large number of diseases and processes, for example brain processes related to Alzheimer's disease, other neurodegenerative diseases, severe mental illnesses, accelerated aging, and vascular disease. Free radicals are molecules containing one or more unpaired orbital electrons, which can increase the molecule's reactivity. Radicals of oxygen are a predominant class of free radicals in the human body. Free oxygen radicals in biology are termed reactive oxygen species (ROS). ROS include the superoxide anion radical, which is a predominant ROS in the brain. ROS are considered important in both acute and chronic inflammation pathways, and can affect multiple metabolic processes and signaling molecules in the brain. Imaging the distribution of ROS is of considerable interest to physicians and other health care professionals.

Dihydroethidine (DHE) is a molecule that can be oxidized by superoxide. When administered peripherally, DHE can enter the brain via the bloodstream and can be oxidized by superoxide. Once oxidized, DHE can be trapped behind the blood brain barrier, and can accumulate there. DHE has been used for visualizing ROS distribution in animal tissue using fluorescence techniques (Quick and Dugan, Ann. Neurology, 49:627-635, 2001; Garbett, N. C., et al., Biophys. J. 87: 3974-3981, 2004). However, health care professionals are in need of tracers that can be used for positron emission tomography (PET) imaging of ROS distribution in vivo.

SUMMARY

The present inventors have developed a series of compounds which can be used as radiolabels for diagnostic imaging, in particular positron emission tomography (PET) imaging of ROS distribution in the tissue of a mammal such as a human. The compounds include analogues of dihydroethidium (DHE) (also known as 2,7-diamino-10-ethyl-9-phenyl-9,10-dihydrophenanthradine, 8-Diamino-5,6-dihydro-5-ethyl-6-phenylphenanthridine and hydroethidine). Analogues of DHE include compounds that are structurally similar to DHE but differ slightly in composition, such as in the replacement of one atom by an atom of a different element or in the presence of a particular functional group.

In some embodiments, the present teachings disclose a radiolabeled compound or salt thereof of structure

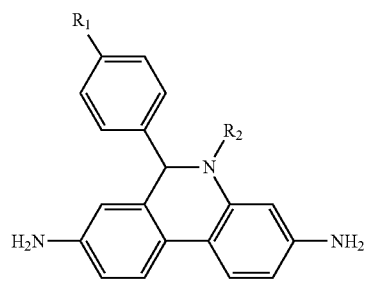

wherein $R_1$ can be H or $O-R_3$, $R_3$ can be $(CH_2)_4CH_3$

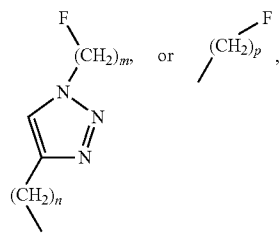

q can be an integer from 0 to 10; n can be an integer from 0 to 3, m can be an integer from 0 to 3, and p can be an integer from 0 to 3, $R_2$ can be methyl or

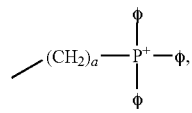

and a can be an integer from 0 to 10. In some configurations, q can be 0.

In further embodiments of the present teachings, the inventors disclose a radiolabeled compound or salt thereof of structure

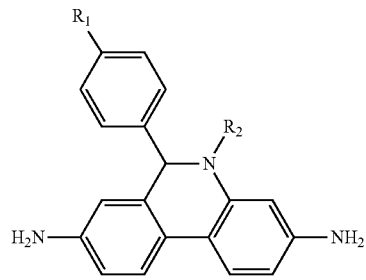

wherein $R_1$ can be H or $O-R_3$; $R_3$ can be $(CH_2)_q-CH_3$,

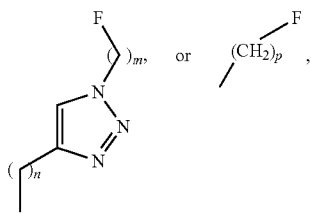

and wherein q can be an integer from 0 to 10; n can be an integer from 0 to 3; m can be an integer from 0 to 3; p can be an integer from 0 to 3; and a can be an integer from 2 to 10. In some configurations, $R_1$ can be H. In some configurations, a $CH_3$ can be an $^{11}CH_3$. In some configurations, $R_3$ can be $(CH_2)_q$—$CH_3$ and q can be 0. In some configurations, $R_3$ can be $^{11}CH_3$. In some configurations, $R_3$ can be

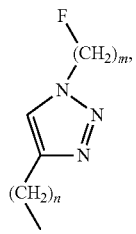

n can be an integer from 0 to 3, and m can be an integer from 0 to 3. In some configurations, $R_1$ can be O—$R_3$, and $R_3$ can be $^{11}CH_3$. In some configurations, F can be $^{18}F$.

In additional embodiments of the present teachings, the inventors disclose methods of imaging ROS in a mammal such as a human. These methods comprise administering to the mammal a radiolabeled compound or salt thereof of structure

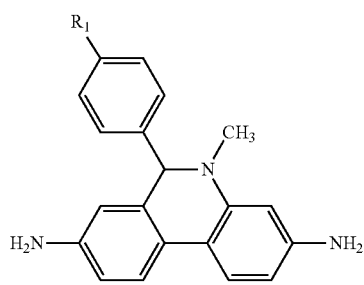

wherein $R_1$ can be H or O—$R_3$, $R_3$ can be $(CH_2)_q CH_3$.

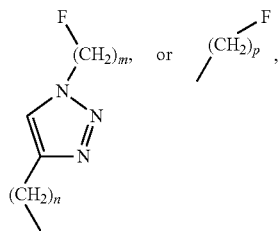

n can be an integer from 0 to 3, m can be an integer from 0 to 3, p can be integer from 0 to 3, and q can be an integer from 0 to 10, and subjecting the mammal to PET scanning.

In some embodiments, a compound of the present teachings can comprise a radioisotope such as a positron-emitting radioisotope, such as $^{18}F$ or $^{11}C$. In some embodiments, a compound of the present teachings can be a radiolabeled compound or salt thereof as disclosed herein, wherein if $R_1$ is H, then the $CH_3$ can be $^{11}CH_3$.

In some embodiments, a compound of the present teachings can be a radiolabeled compound or salt thereof as disclosed herein, wherein if $R_1$ is O—$R_3$, and q=0, then $R_3$ can be $^{11}CH_3$.

In some embodiments, a compound of the present teachings can be a radiolabeled compound or salt thereof as disclosed herein, wherein if $R_1$ can be O—$R_3$, and $R_3$ can be a fluorinated moiety such as

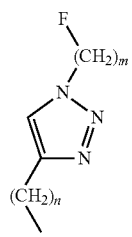

wherein n can be an integer from 0 to 3, m can be an integer from 0 to 3, the F can be an $^{18}F$. In some configurations, n can be 1 and m can be 2.

In some embodiments, a compound of the present teachings can be a radiolabeled compound or salt thereof as disclosed herein, wherein if $R_1$ is O—$R_3$, then $R_3$ can be a fluorinated moiety such as

wherein p can be an integer from 0 to 3, and the F can be an $^{18}F$. In some configurations, p can be 2.

In various aspects of the above embodiments, a radiolabeled compound or salt thereof can be a molecular species such a

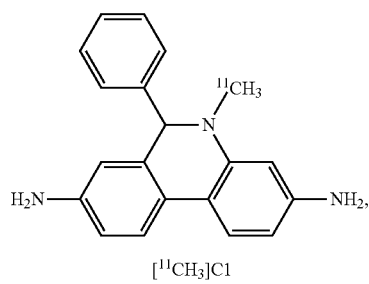

[$^{11}CH_3$]C1

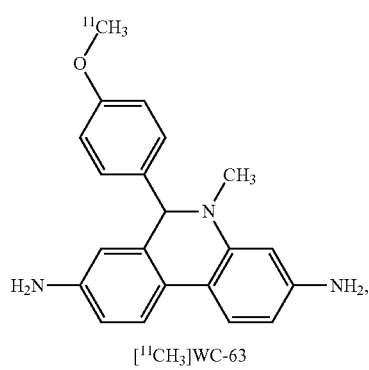

[$^{11}CH_3$]WC-63

-continued

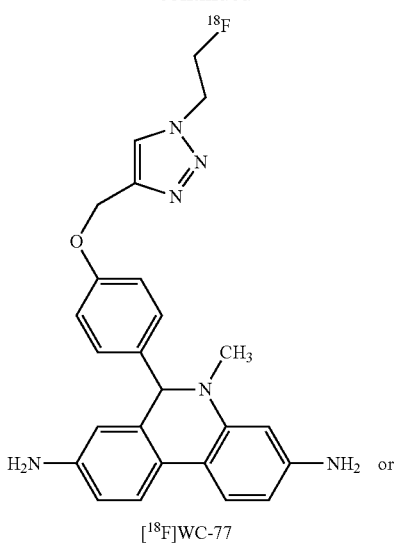

[$^{18}$F]WC-77

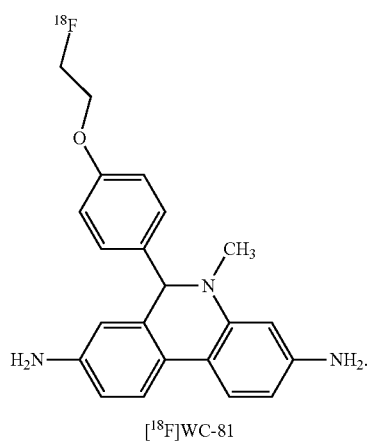

[$^{18}$F]WC-81

The present teachings also include various analogues of dihydroethidium (DHE) that can serve as intermediates or precursors in syntheses of the radiolabeled compounds disclosed herein.

The present teachings also include methods of synthesis of radiolabeled compounds described herein, as well as synthesis of various intermediates and precursors.

The present teachings include, without limitation, the following aspects:

1. A radiolabeled compound or salt thereof of structure

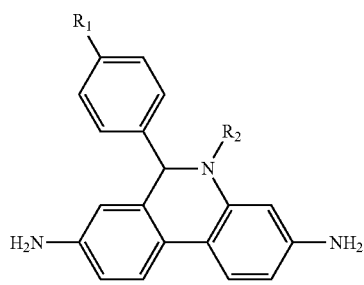

wherein $R_1$ is H or O—$R_3$, $R_3$ is $(CH_2)_q CH_3$.

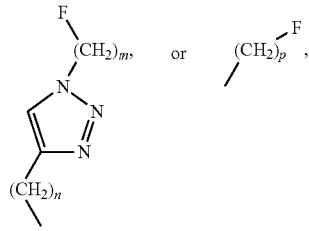

q is an integer from 0 to 10; n is an integer from 0 to 3, m is an integer from 0 to 3, and p is an integer from 0 to 3, $R_2$ is methyl or

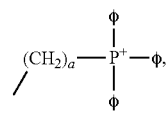

and a is an integer from 0 to 10, wherein at least one atom is a radioisotope.

2. A radiolabeled compound or salt thereof in accordance with aspect 1, wherein the radioisotope is a positron-emitting radioisotope.

3. A radiolabeled compound or salt thereof in accordance with aspect 1, wherein $R_1$ is H.

4. A radiolabeled compound or salt thereof in accordance with aspect 3, wherein the $CH_3$ is an $^{11}CH_3$.

5. A radiolabeled compound or salt thereof in accordance with aspect 1, wherein $R_3$ is $(CH_2)_q$—$CH_3$ and q is 0.

6. A radiolabeled compound or salt thereof in accordance with aspect 5, wherein $R_3$ is $^{11}CH_3$.

7. A radiolabeled compound or salt thereof in accordance with aspect 1, wherein $R_3$ is

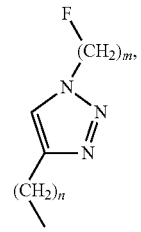

n is an integer from 0 to 3, and m is an integer from 0 to 3.

8. A radiolabeled compound or salt thereof in accordance with aspect 1, wherein $R_1$ is O—$R_3$, $R_3$ is $CH_3$.

9. A radiolabeled compound or salt thereof in accordance with aspect 8, wherein $R_1$ is O—$R_3$, wherein $R_3$ is $^{11}CH_3$.

10. A radiolabeled compound or salt thereof in accordance with aspect 1, wherein $R_1$ is O—$R_3$, $R_3$ is

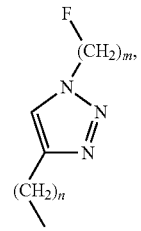

n is an integer from 0 to 3 and m is an integer from 0 to 3, and F is $^{18}$F.

11. A radiolabeled compound or salt thereof in accordance with aspect 10, wherein n is 1.
12. A radiolabeled compound or salt thereof in accordance with aspect 10, wherein m is 2.
13. A radiolabeled compound or salt thereof in accordance with aspect 10, wherein n is 1 and m is 2.
14. A radiolabeled compound or salt thereof in accordance with aspect 1, wherein $R_3$ is

p is an integer from 0 to 3 and F is $^{18}$F.

15. A radiolabeled compound or salt thereof in accordance with aspect 13, wherein p is 2.
16. A radiolabeled compound or salt thereof in accordance with aspect 1, wherein the compound is selected from the group consisting of

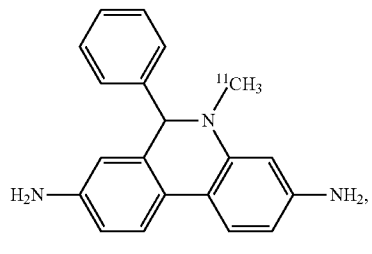

[$^{11}$CH$_3$]C1

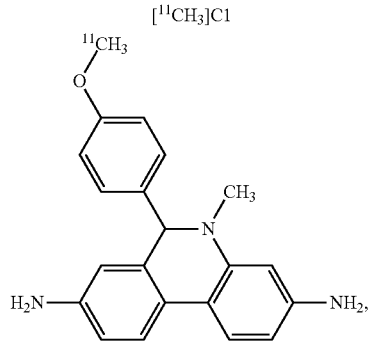

[$^{11}$CH$_3$]WC-63

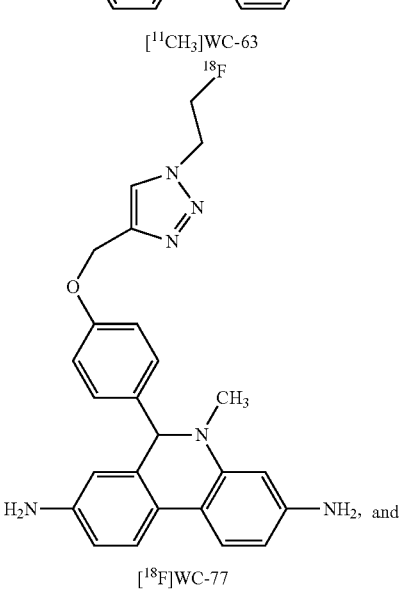

[$^{18}$F]WC-77

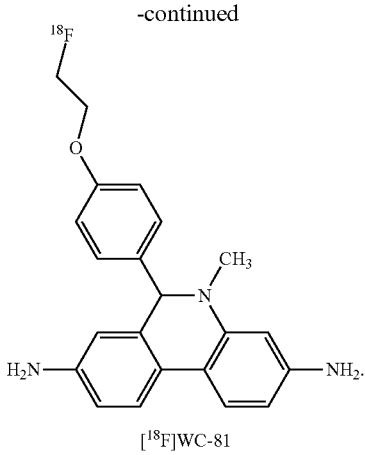

[$^{18}$F]WC-81

17. A method of imaging reactive oxygen species (ROS) distribution in a mammal, the method comprising:
   administering to the mammal a compound or salt thereof, of any one of aspects 1-15; and
   subjecting the mammal to PET scanning.

18. A method of synthesizing

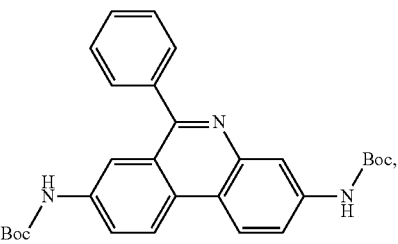 [SMILES: CC(C)(C)OC(=O)Nc1ccc2c(c1)nc(-c1ccccc1)c1cc(NC(=O)OC(C)(C)C)ccc12]

comprising contacting

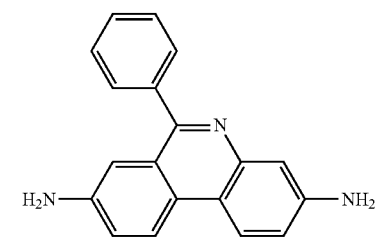 [SMILES: Nc1ccc2c(c1)nc(-c1ccccc1)c1cc(N)ccc12]

with (Boc)$O_2$.

19. A method of synthesizing

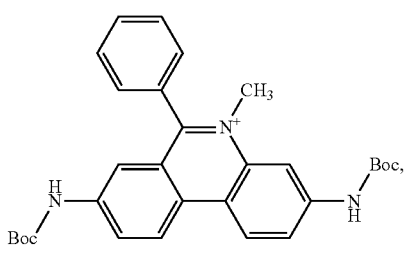 [SMILES: C[n+]1c(-c2ccccc2)c2cc(NC(=O)OC(C)(C)C)ccc2c2ccc(NC(=O)OC(C)(C)C)cc21]

comprising contacting
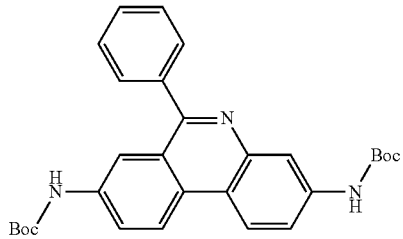 [SMILES: CC(C)(C)OC(=O)Nc1ccc2c(c1)nc(-c1ccccc1)c1cc(NC(=O)OC(C)(C)C)ccc12]
with CH₃I and THF.
20. A method of synthesizing
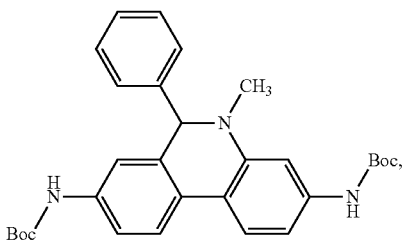 [SMILES: CN1c2cc(NC(=O)OC(C)(C)C)ccc2-c2ccc(NC(=O)OC(C)(C)C)cc2C1c1ccccc1]
comprising contacting
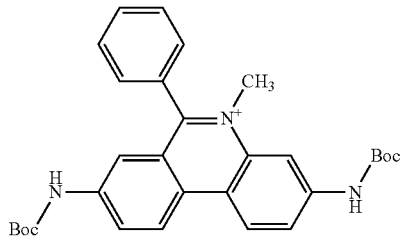 [SMILES: C[n+]1c(-c2ccccc2)c2cc(NC(=O)OC(C)(C)C)ccc2c2ccc(NC(=O)OC(C)(C)C)cc21]
with NaBH₃CN.
21. A method of synthesizing
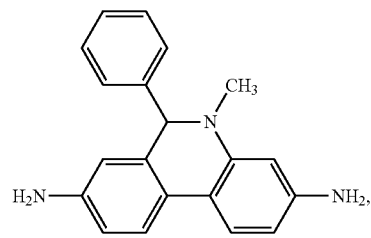 [SMILES: CN1c2cc(N)ccc2-c2ccc(N)cc2C1c1ccccc1]
comprising contacting with EtOAc/HCl.
22. A method of synthesizing
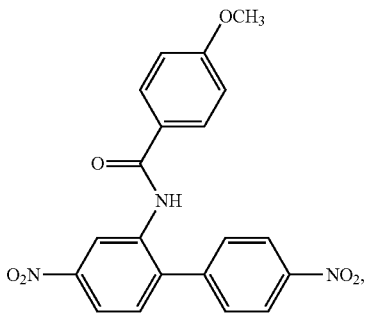 [SMILES: COc1ccc(C(=O)Nc2cc([N+](=O)[O-])ccc2-c2ccc([N+](=O)[O-])cc2)cc1]
comprising contacting
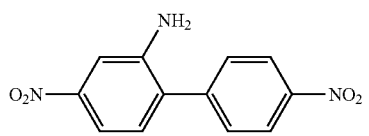 [SMILES: Nc1cc([N+](=O)[O-])ccc1-c1ccc([N+](=O)[O-])cc1]
with 4-methoxybenzoyl chloride and chlorobenzene.
23. A method of synthesizing
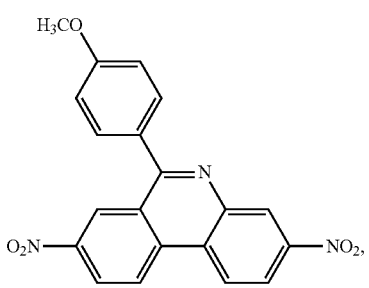 [SMILES: COc1ccc(-c2nc3cc([N+](=O)[O-])ccc3c3ccc([N+](=O)[O-])cc23)cc1]
comprising contacting
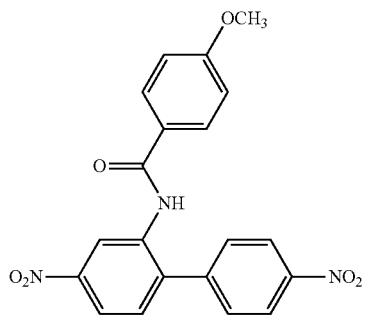 [SMILES: COc1ccc(C(=O)Nc2cc([N+](=O)[O-])ccc2-c2ccc([N+](=O)[O-])cc2)cc1]
with POCl₃.

24. A method of synthesizing
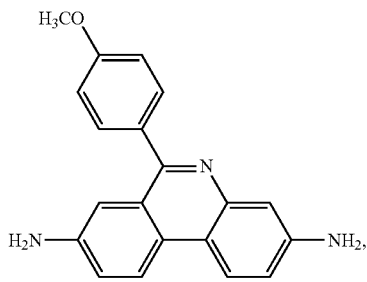
comprising contacting
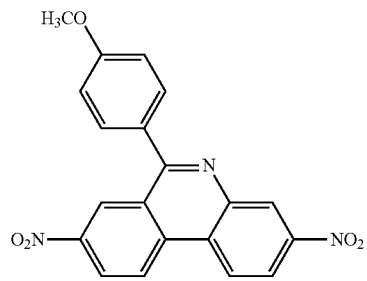 [SMILES: COc1ccc(-c2nc3cc([N+](=O)[O-])ccc3c3ccc([N+](=O)[O-])cc23)cc1]
with HCOONH$_4$, Pd(OH)$_2$/C.
25. A method of synthesizing
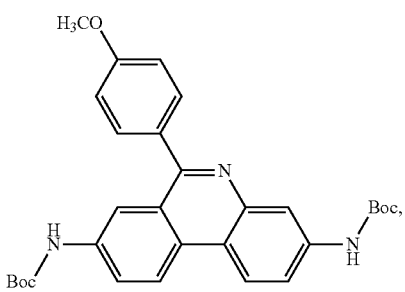 [SMILES: COc1ccc(-c2nc3cc(NC(=O)OC(C)(C)C)ccc3c3ccc(NC(=O)OC(C)(C)C)cc23)cc1]
comprising contacting
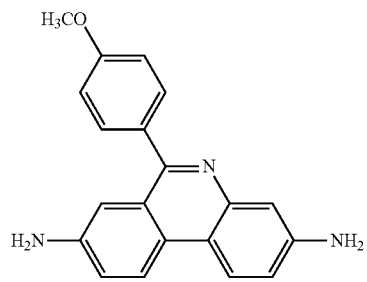 [SMILES: COc1ccc(-c2nc3cc(N)ccc3c3ccc(N)cc23)cc1]
with (Boc)$_2$O.
26. A method for synthesizing
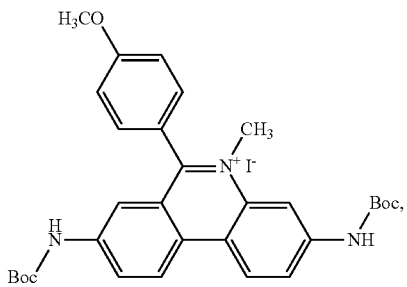
comprising contacting
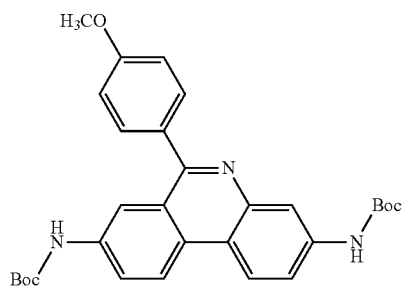 [SMILES: COc1ccc(-c2nc3cc(NC(=O)OC(C)(C)C)ccc3c3ccc(NC(=O)OC(C)(C)C)cc23)cc1]
with CH$_3$I, THF.
27. A method of synthesizing
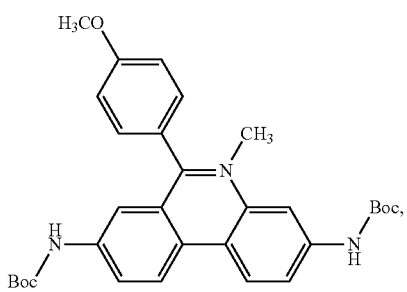
comprising contacting
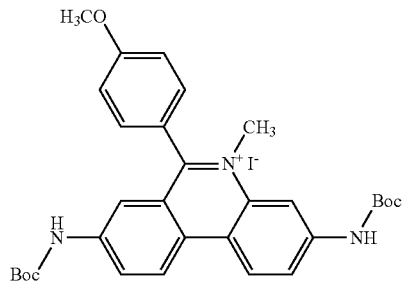
with NaBH$_3$CN.

28. A method of synthesizing
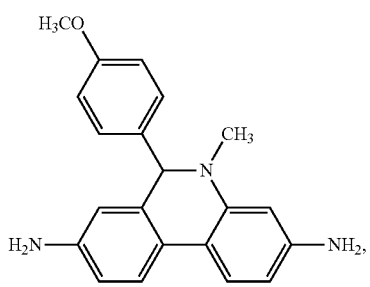 [SMILES: COc1ccc(C2c3cc(N)ccc3-c3ccc(N)cc3N2C)cc1]
comprising contacting
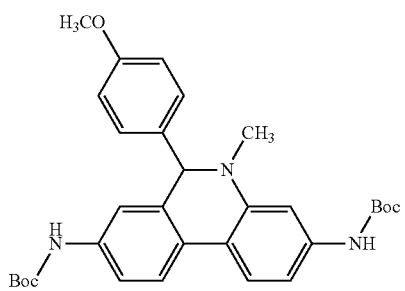 [SMILES: COc1ccc(C2c3cc(NC(=O)OC(C)(C)C)ccc3-c3ccc(NC(=O)OC(C)(C)C)cc3N2C)cc1]
with HCl.
29. A method of synthesizing
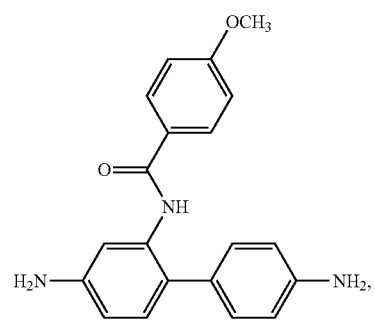
comprising contacting
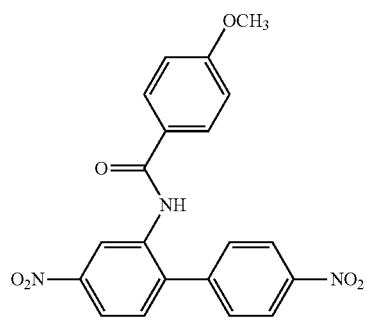 [SMILES: COc1ccc(C(=O)Nc2cc([N+](=O)[O-])ccc2-c2ccc([N+](=O)[O-])cc2)cc1]
with HCOONH₄ and Pd(OH)₂/C.
30. A method of synthesizing
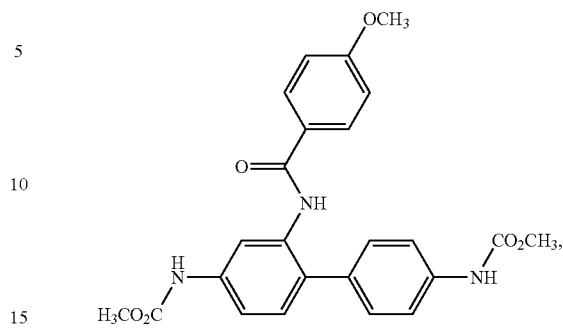
comprising contacting
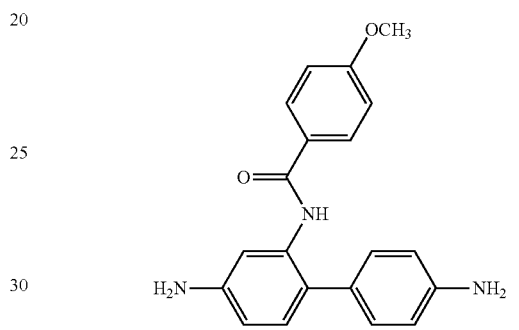
with ClCOOCH₃.
31. A method of synthesizing
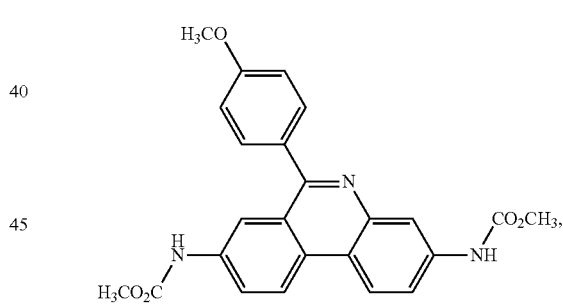
comprising contacting
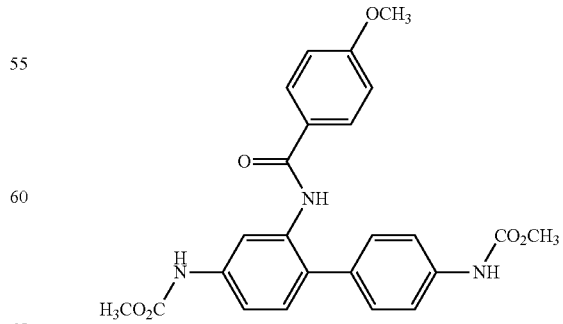
with POCl₃.

32. A method of synthesizing
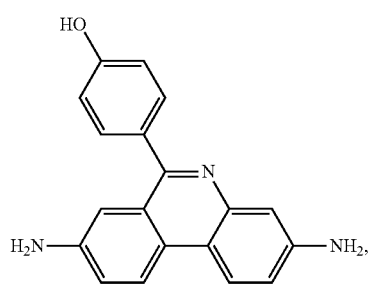 [SMILES: Nc1ccc2c(c1)nc(-c1ccc(O)cc1)c1cc(N)ccc12]
comprising contacting
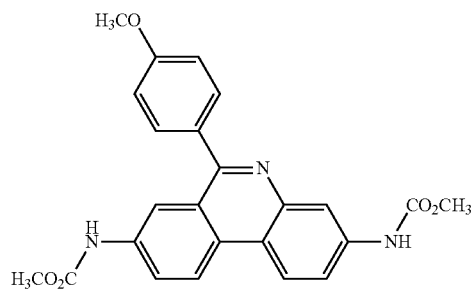 [SMILES: COC(=O)Nc1ccc2c(c1)nc(-c1ccc(OC)cc1)c1cc(NC(=O)OC)ccc12]
with HBr.
33. A method of synthesizing
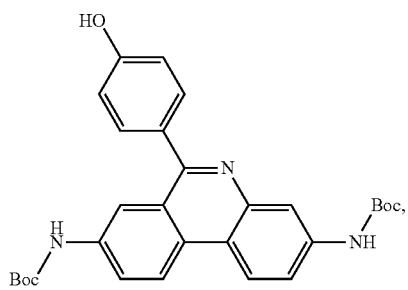 [SMILES: CC(C)(C)OC(=O)Nc1ccc2c(c1)nc(-c1ccc(O)cc1)c1cc(NC(=O)OC(C)(C)C)ccc12]
comprising contacting
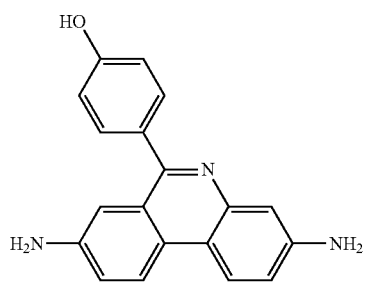 [SMILES: Nc1ccc2c(c1)nc(-c1ccc(O)cc1)c1cc(N)ccc12]
with (Boc)$_2$O.
34. A method of synthesizing
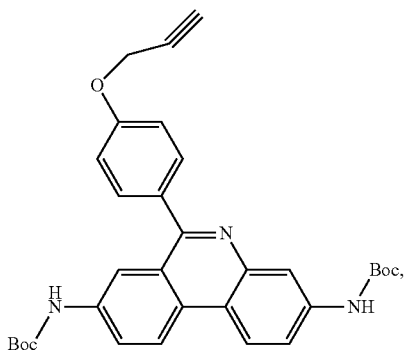 [SMILES: C#CCOc1ccc(-c2nc3cc(NC(=O)OC(C)(C)C)ccc3c3ccc(NC(=O)OC(C)(C)C)cc23)cc1]
comprising contacting
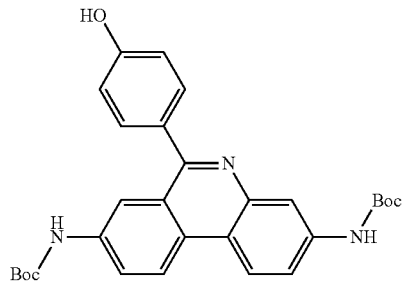 [SMILES: CC(C)(C)OC(=O)Nc1ccc2c(c1)nc(-c1ccc(O)cc1)c1cc(NC(=O)OC(C)(C)C)ccc12]
with 3-bromoprop-1-yne K$_2$CO$_3$, acetone.
35. A method of synthesizing
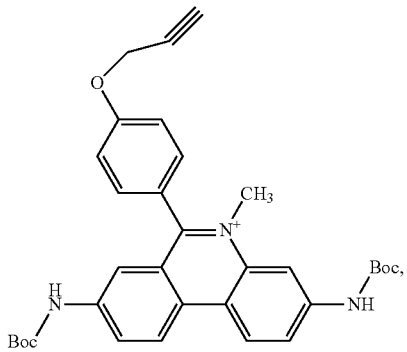 [SMILES: C#CCOc1ccc(-c2c3cc(NC(=O)OC(C)(C)C)ccc3c3ccc(NC(=O)OC(C)(C)C)cc3[n+]2C)cc1]
comprising contacting
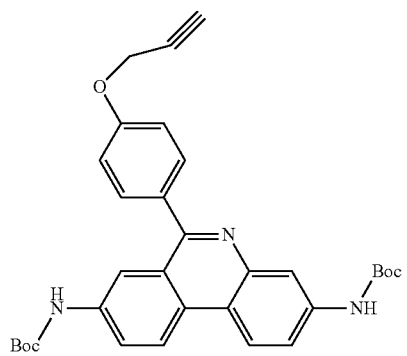 [SMILES: C#CCOc1ccc(-c2nc3cc(NC(=O)OC(C)(C)C)ccc3c3ccc(NC(=O)OC(C)(C)C)cc23)cc1]
with CH$_3$I, THF.

36. A method of synthesizing
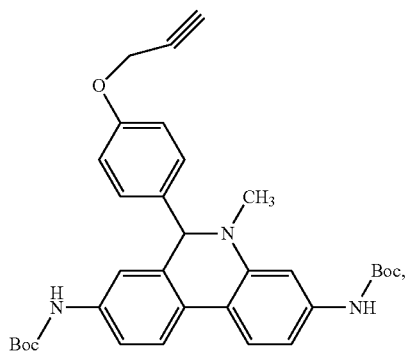 [SMILES: C#CCOc1ccc(C2c3cc(NC(=O)OC(C)(C)C)ccc3-c3ccc(NC(=O)OC(C)(C)C)cc3N2C)cc1]
comprising contacting
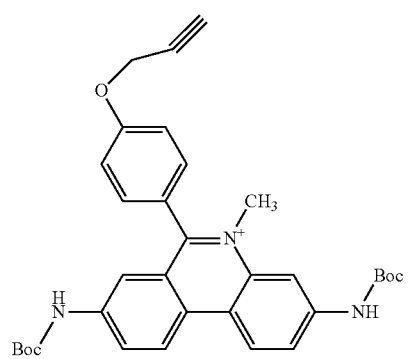 [SMILES: C#CCOc1ccc(-c2c3cc(NC(=O)OC(C)(C)C)ccc3c3ccc(NC(=O)OC(C)(C)C)cc3[n+]2C)cc1]
with NaBH₃CN.
37. A method of synthesizing
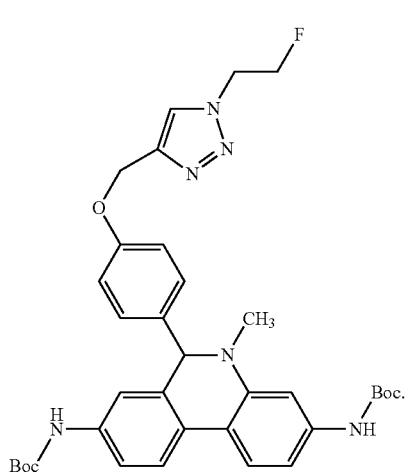 [SMILES: CN1c2cc(NC(=O)OC(C)(C)C)ccc2-c2ccc(NC(=O)OC(C)(C)C)cc2C1c1ccc(OCc2cn(CCF)nn2)cc1]
comprising contacting
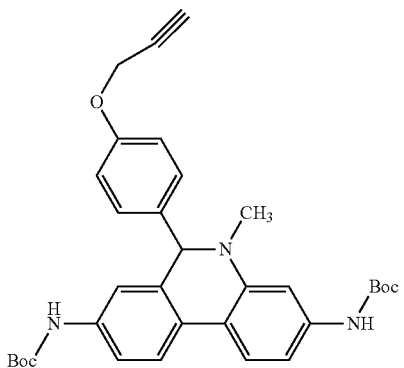 [SMILES: C#CCOc1ccc(C2c3cc(NC(=O)OC(C)(C)C)ccc3-c3ccc(NC(=O)OC(C)(C)C)cc3N2C)cc1]
with N₃CH₂CH₂F, CuSO₄, sodium ascorbate, DMF.
38. A method of synthesizing
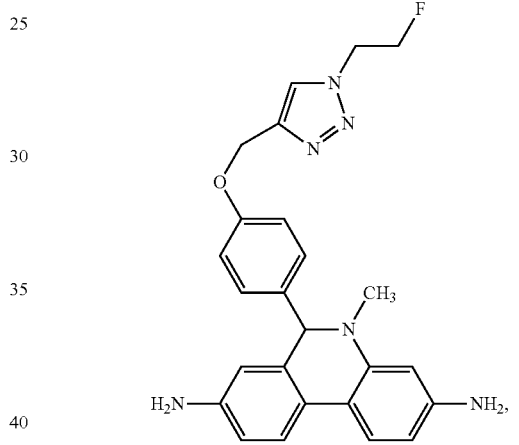
comprising contacting
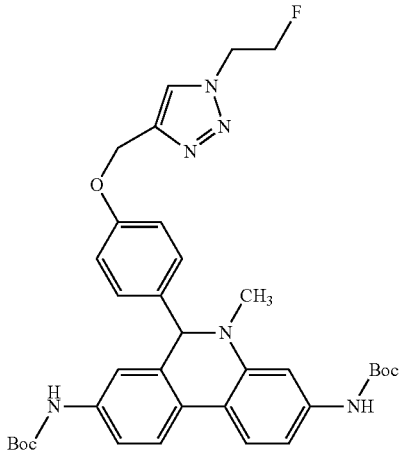 [SMILES: CN1c2cc(NC(=O)OC(C)(C)C)ccc2-c2ccc(NC(=O)OC(C)(C)C)cc2C1c1ccc(OCc2cn(CCF)nn2)cc1]
with EtOAc/HCl.

39. A method of synthesizing
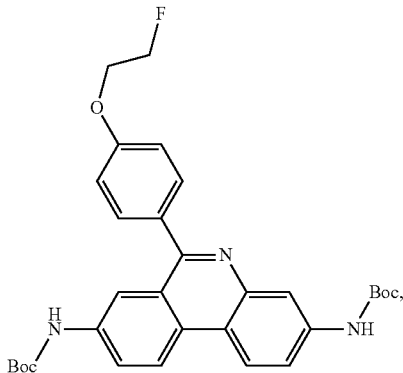 [SMILES: CC(C)(C)OC(=O)Nc1ccc2c(c1)nc(-c1ccc(OCCF)cc1)c1cc(NC(=O)OC(C)(C)C)ccc12]
comprising contacting
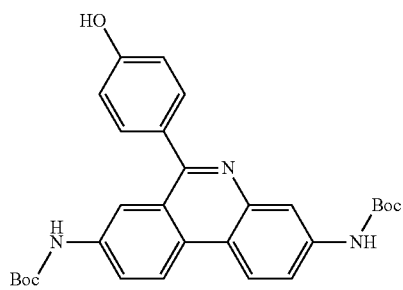 [SMILES: CC(C)(C)OC(=O)Nc1ccc2c(c1)nc(-c1ccc(O)cc1)c1cc(NC(=O)OC(C)(C)C)ccc12]
with BrCH$_2$CH$_2$F, K$_2$CO$_3$, acetone.
40. A method of synthesizing
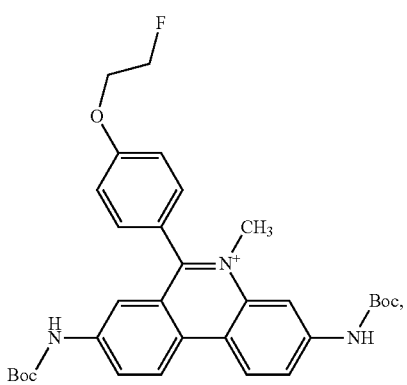 [SMILES: C[n+]1c(-c2ccc(OCCF)cc2)c2cc(NC(=O)OC(C)(C)C)ccc2c2ccc(NC(=O)OC(C)(C)C)cc21]
comprising contacting
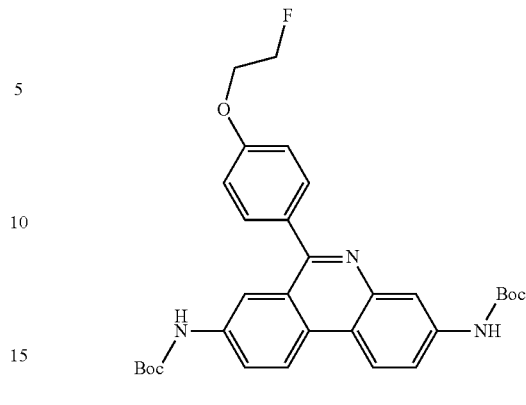
with CH$_3$I, THF.
41. A method of synthesizing
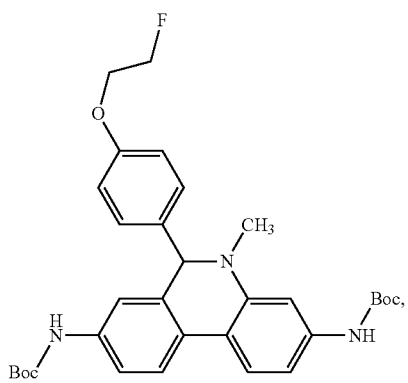 [SMILES: CN1c2cc(NC(=O)OC(C)(C)C)ccc2-c2ccc(NC(=O)OC(C)(C)C)cc2C1c1ccc(OCCF)cc1]
comprising contacting
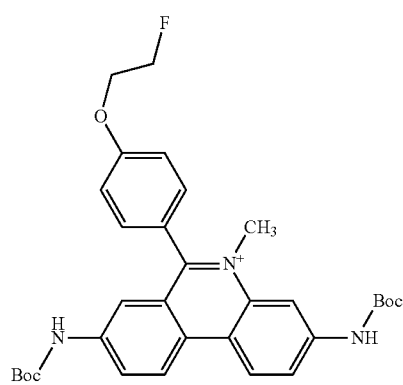
with NaBH$_3$CN.

42. A method of synthesizing
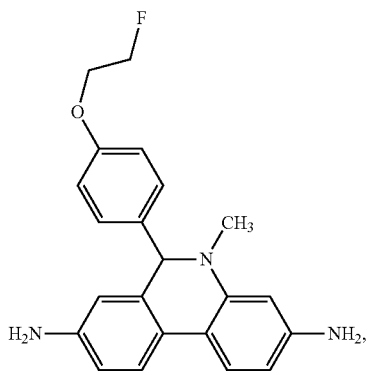 [SMILES: CN1c2cc(N)ccc2-c2ccc(N)cc2C1c1ccc(OCCF)cc1]
comprising contacting
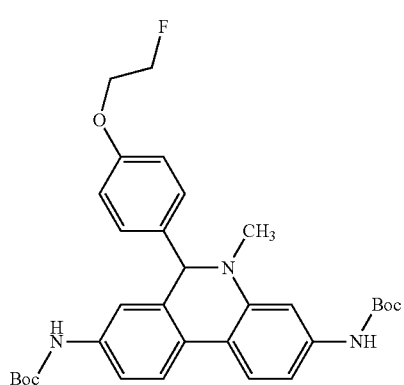
with EtOAc/HCl.
43. A method of synthesizing
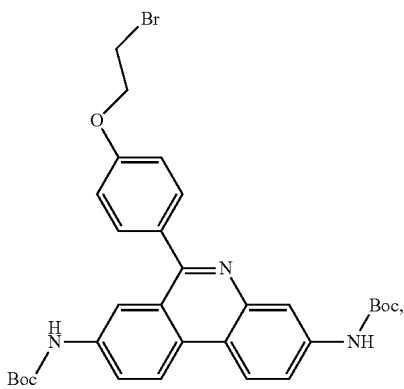 [SMILES: CC(C)(C)OC(=O)Nc1ccc2c(c1)nc(-c1ccc(OCCBr)cc1)c1cc(NC(=O)OC(C)(C)C)ccc12]
comprising contacting
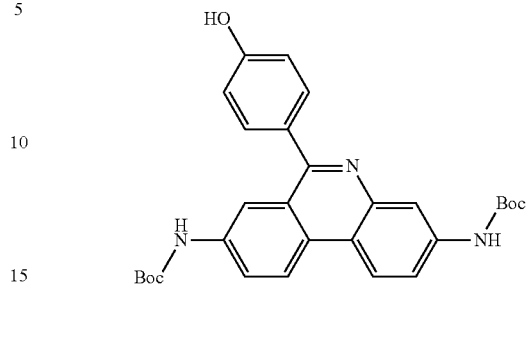
with BrCH$_2$CH$_2$Br, acetone.
44. A method of synthesizing
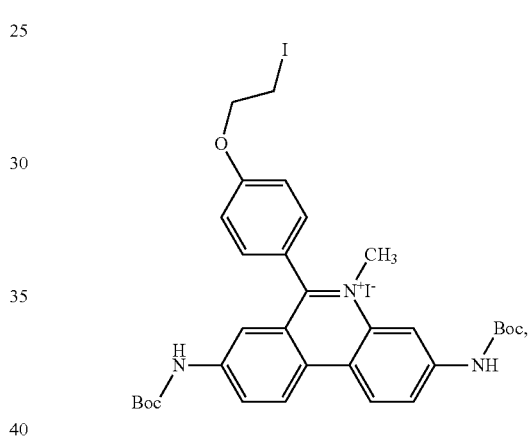
comprising contacting
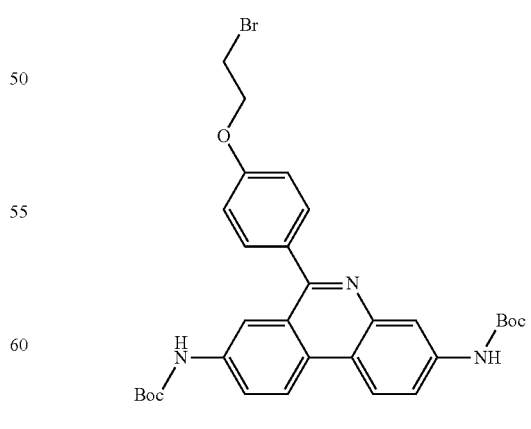
with CH$_3$I, THF.

45. A method of synthesizing
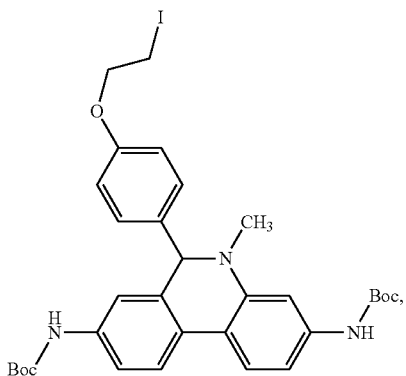
comprising contacting
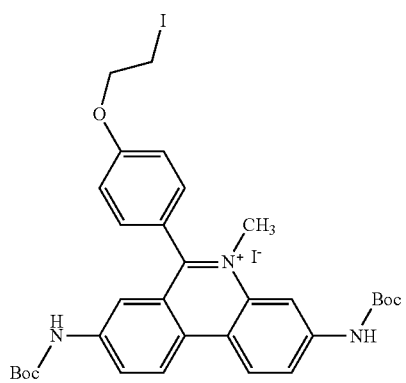 [SMILES: C[n+]1c(-c2ccc(OCCI)cc2)c2cc(NC(=O)OC(C)(C)C)ccc2c2ccc(NC(=O)OC(C)(C)C)cc21 ; [I-]]
with NaBH₃CN.
46. A method of synthesizing
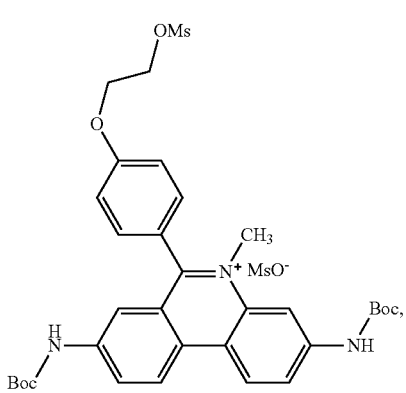 [SMILES: "MsO-" ; C[n+]1c(-c2ccc(OCCOS(C)(=O)=O)cc2)c2cc(NC(=O)OC(C)(C)C)ccc2c2ccc(NC(=O)OC(C)(C)C)cc21]
comprising contacting
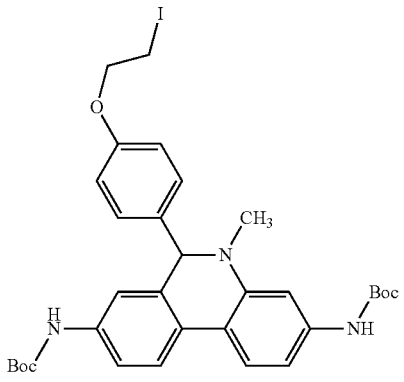
with AgOMs, CH₃CN.
47. A method of synthesizing
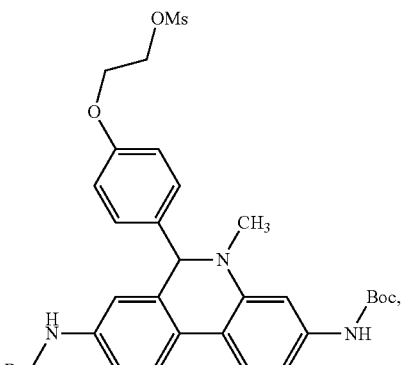
comprising contacting
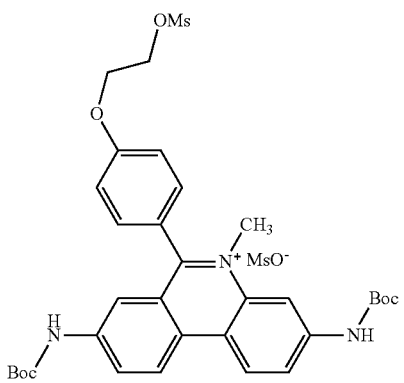 [SMILES: "MsO-" ; C[n+]1c(-c2ccc(OCCOS(C)(=O)=O)cc2)c2cc(NC(=O)OC(C)(C)C)ccc2c2ccc(NC(=O)OC(C)(C)C)cc21]
with NaBH₃CN.

48. A method of synthesizing
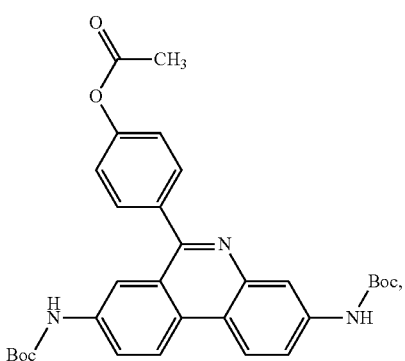 [SMILES: CC(=O)Oc1ccc(-c2nc3cc(NC(=O)OC(C)(C)C)ccc3c3ccc(NC(=O)OC(C)(C)C)cc23)cc1]
comprising contacting
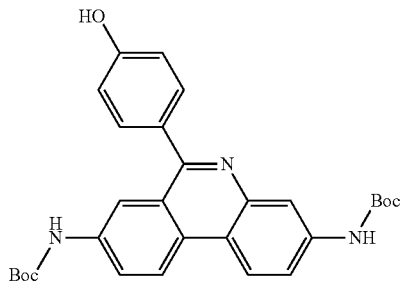 [SMILES: CC(C)(C)OC(=O)Nc1ccc2c(c1)nc(-c1ccc(O)cc1)c1cc(NC(=O)OC(C)(C)C)ccc12]
with Ac₂O.
49. A method of synthesizing
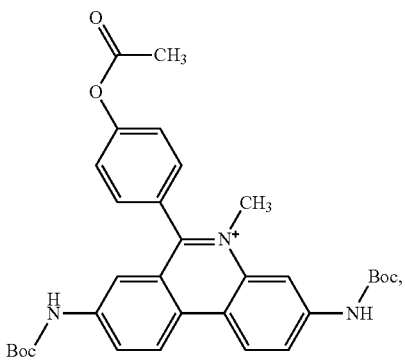 [SMILES: CC(=O)Oc1ccc(-c2c3cc(NC(=O)OC(C)(C)C)ccc3c3ccc(NC(=O)OC(C)(C)C)cc3[n+]2C)cc1]
comprising contacting
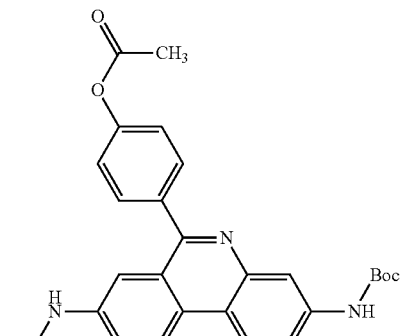
with CH₃I, THF.
50. A method of synthesizing
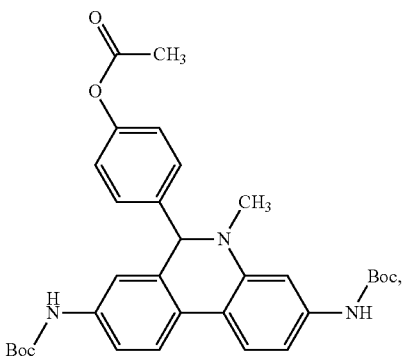 [SMILES: CC(=O)Oc1ccc(C2c3cc(NC(=O)OC(C)(C)C)ccc3-c3ccc(NC(=O)OC(C)(C)C)cc3N2C)cc1]
comprising contacting
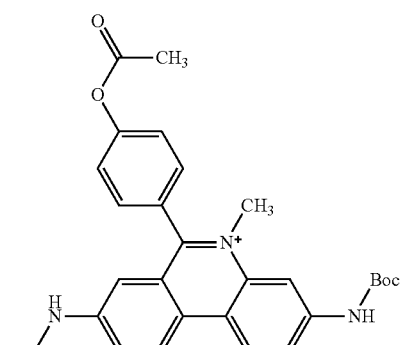
with NaBH₃CN.

51. A method of synthesizing
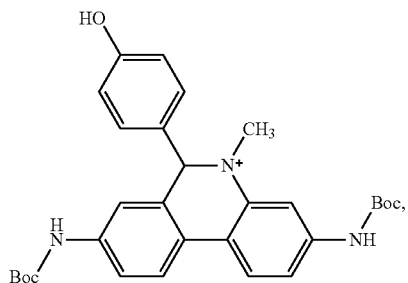 [SMILES: C[NH+]1c2cc(NC(=O)OC(C)(C)C)ccc2-c2ccc(NC(=O)OC(C)(C)C)cc2C1c1ccc(O)cc1]
comprising contacting
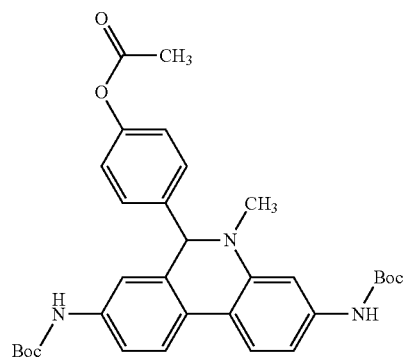 [SMILES: CC(=O)Oc1ccc(C2c3cc(NC(=O)OC(C)(C)C)ccc3-c3ccc(NC(=O)OC(C)(C)C)cc3N2C)cc1]
with LiOH, MeOH.
52. A method of synthesizing
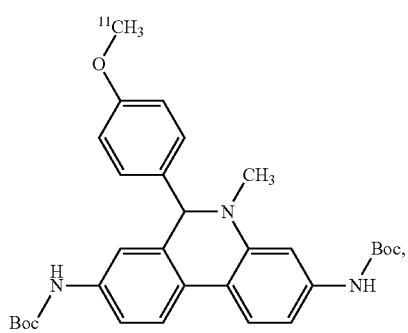 [SMILES: CN1c2cc(NC(=O)OC(C)(C)C)ccc2-c2ccc(NC(=O)OC(C)(C)C)cc2C1c1ccc(O[11CH3])cc1]
comprising contacting
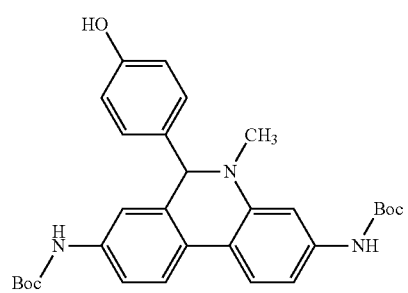 [SMILES: CN1c2cc(NC(=O)OC(C)(C)C)ccc2-c2ccc(NC(=O)OC(C)(C)C)cc2C1c1ccc(O)cc1]
with $^{11}CH_3I$, $K_2CO_3$.
53. A method of synthesizing
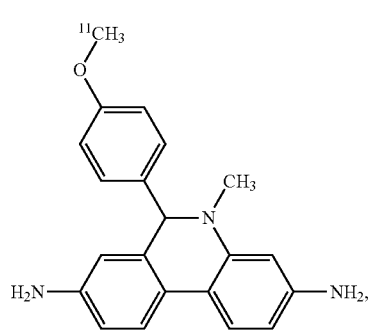 [SMILES: CN1c2cc(N)ccc2-c2ccc(N)cc2C1c1ccc(O[11CH3])cc1]
comprising contacting
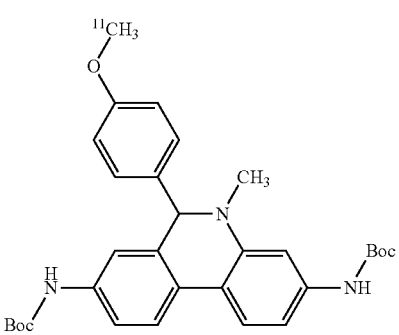 [SMILES: CN1c2cc(NC(=O)OC(C)(C)C)ccc2-c2ccc(NC(=O)OC(C)(C)C)cc2C1c1ccc(O[11CH3])cc1]
with EtOAc/HCl.
54. A method of synthesizing
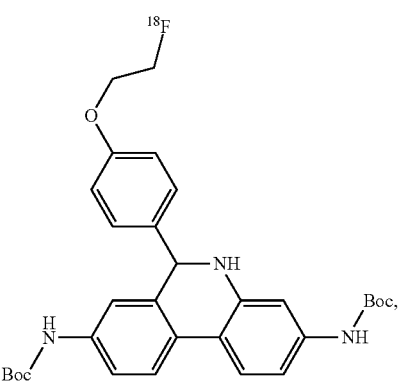 [SMILES: CC(C)(C)OC(=O)Nc1ccc2c(c1)NC(c1ccc(OCC[18F])cc1)c1cc(NC(=O)OC(C)(C)C)ccc1-2]

comprising contacting
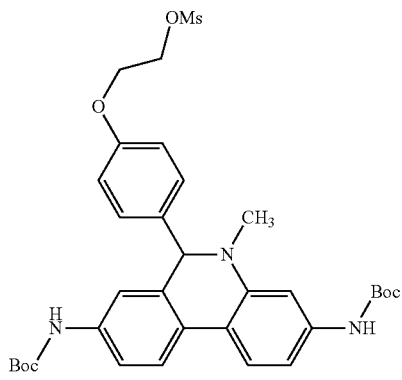 [SMILES: CN1c2cc(NC(=O)OC(C)(C)C)ccc2-c2ccc(NC(=O)OC(C)(C)C)cc2C1c1ccc(OCCOS(C)(=O)=O)cc1]
with [$^{18}$F]KF, K$_{222}$, K$_{222}$ is Kryptofix 222® (E. Merck, Darmstadt Germany), i.e., 4,7,13,16,21,24-Hexaoxa-1,10-diazabicyclo[8.8.8]-hexacosane C$_{18}$H$_{36}$N$_2$O$_6$.
55. A method of synthesizing
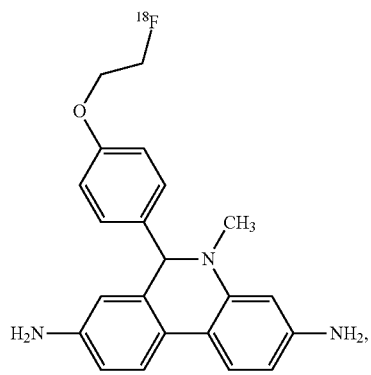 [SMILES: CN1c2cc(N)ccc2-c2ccc(N)cc2C1c1ccc(OCC[18F])cc1]
comprising contacting
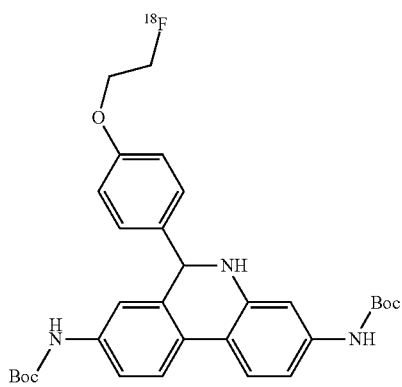 [SMILES: CC(C)(C)OC(=O)Nc1ccc2c(c1)NC(c1ccc(OCC[18F])cc1)c1cc(NC(=O)OC(C)(C)C)ccc1-2]
with EtOAc/HCl.
56. A method of synthesizing
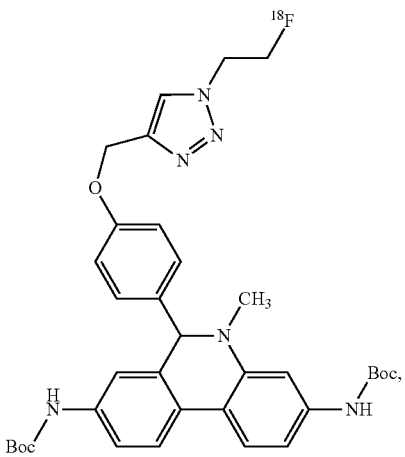 [SMILES: CN1c2cc(NC(=O)OC(C)(C)C)ccc2-c2ccc(NC(=O)OC(C)(C)C)cc2C1c1ccc(OCc2cn(CC[18F])nn2)cc1]
comprising contacting
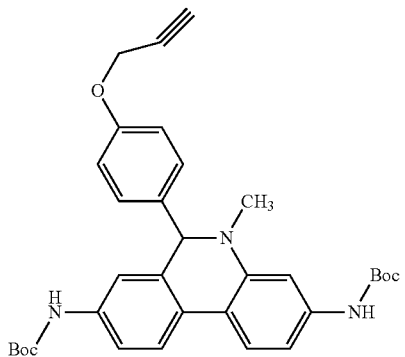 [SMILES: C#CCOc1ccc(C2c3cc(NC(=O)OC(C)(C)C)ccc3-c3ccc(NC(=O)OC(C)(C)C)cc3N2C)cc1]
with $^{18}$FCH$_2$CH$_2$N$_3$, CuSO$_4$, sodium ascorbate, DMF.
57. A method of synthesizing
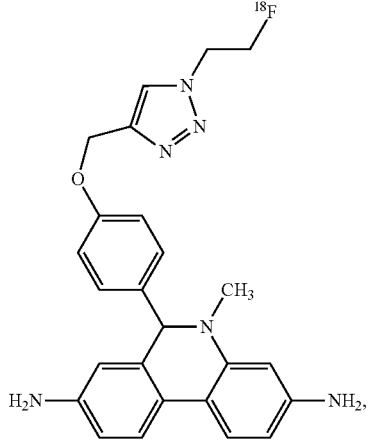 [SMILES: CN1c2cc(N)ccc2-c2ccc(N)cc2C1c1ccc(OCc2cn(CC[18F])nn2)cc1]

comprising contacting
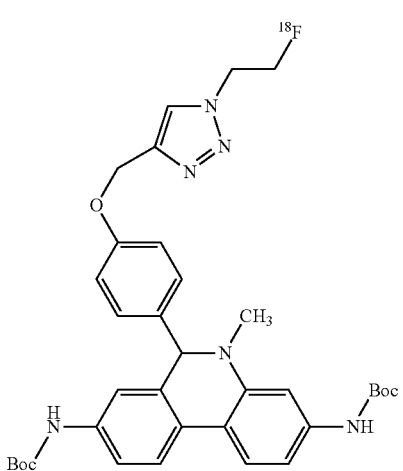 [SMILES: CN1c2cc(NC(=O)OC(C)(C)C)ccc2-c2ccc(NC(=O)OC(C)(C)C)cc2C1c1ccc(OCc2cn(CC[18F])nn2)cc1]
with EtOAc/HCl.
58. A method of synthesizing
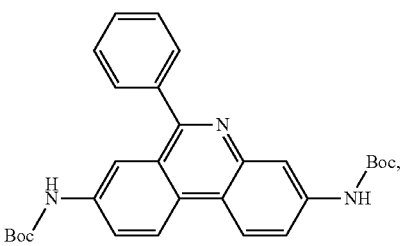 [SMILES: CC(C)(C)OC(=O)Nc1ccc2c(c1)nc(-c1ccccc1)c1cc(NC(=O)OC(C)(C)C)ccc12]
comprising contacting
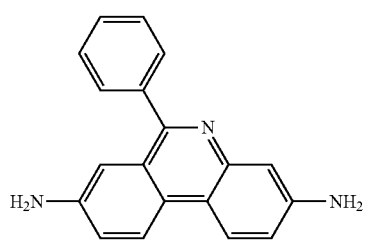 [SMILES: Nc1ccc2c(c1)nc(-c1ccccc1)c1cc(N)ccc12]
with (Boc)₂O.
59. A method of synthesizing
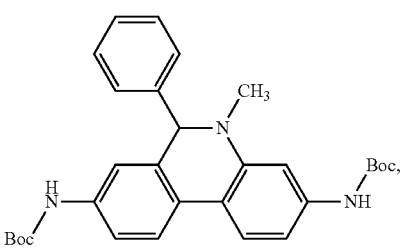 [SMILES: CN1c2cc(NC(=O)OC(C)(C)C)ccc2-c2ccc(NC(=O)OC(C)(C)C)cc2C1c1ccccc1]
comprising contacting
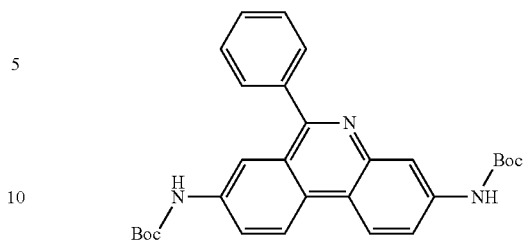
with CH₃I, followed by NaBH₃CN.
60. A method of synthesizing
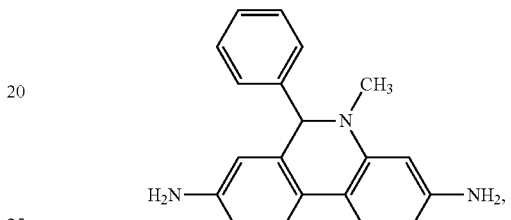
comprising contacting
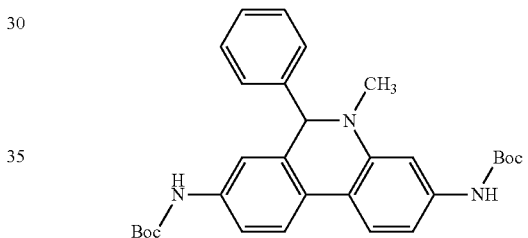
with HCl.
61. A method of synthesizing
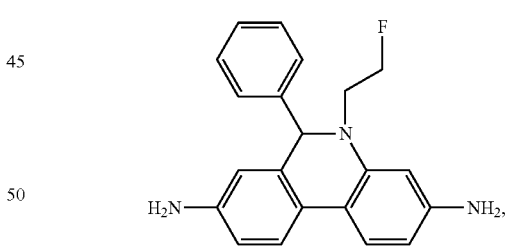
comprising contacting
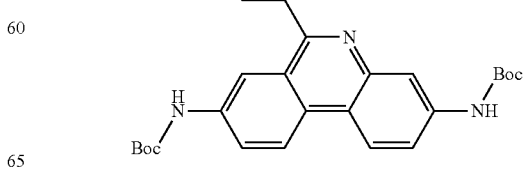
with BrCH₂CH₂F, followed by NaBH₃CN, followed by HCl.

BRIEF DESCRIPTION OF THE DRAWINGS

In FIG. 3, the data for compounds WC-63, WC-77 and WC-81 are labeled PET63, PET77 and PET82, respectively.

In FIG. 4, panel G is an enlarged image of panel B.

In FIG. 8, all images are calibrated to the same scale.

DETAILED DESCRIPTION

Figure 1:
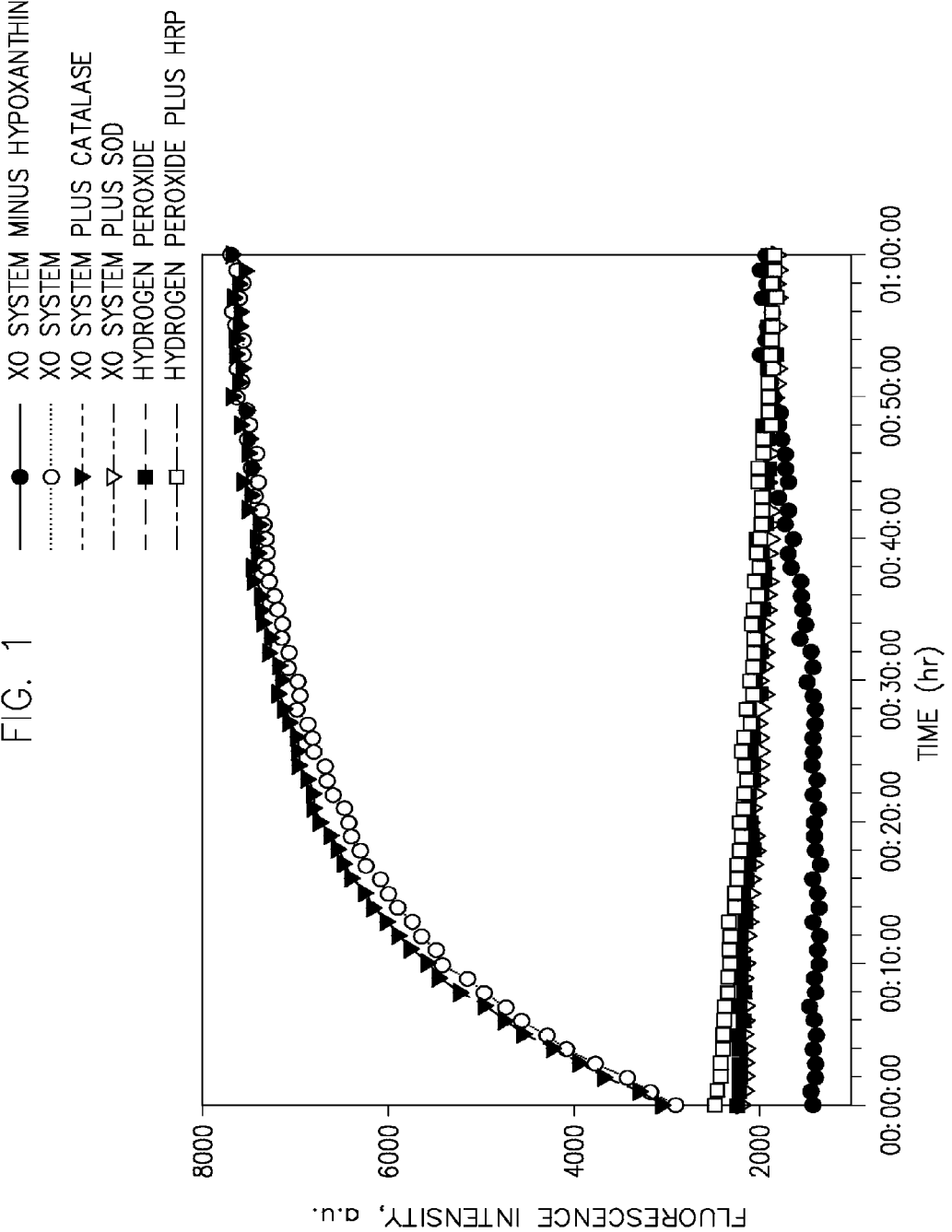
FIG. 1 illustrates the fluorescence intensity over time in a platereader study of oxidation rate of compound C1. The X-axis scale is in hours:minutes:seconds. The fluorescence intensity is measured in arbitrary units (a.u.).

The present inventors disclose herein a series of compounds, including radiolabeled compounds, that can be used as tracers for imaging distribution of reactive oxygen species in a mammalian subject such as a human. Distribution of ROS using a compound disclosed herein as a tracer can be determined by fluorescence imaging, or by positron emission topography (PET) imaging. In some embodiments, a compound can comprise a radioisotope, such as a positron emitter. Accordingly, a compound of the present teachings can comprise a radioisotope such as $^{18}F$ or $^{11}C$.

In some aspects, the inventors provide methods of imaging ROS in tissue in a human or other animal subject such as a mammalian subject. These methods comprise administering to the subject a radiolabeled compound, and imaging distribution of the radiolabel by PET scanning. In some configurations, the PET scanning can yield an image which can then be interpreted by a medical professional, such as a physician.

Without limitation, a radiolabeled compound of the present teachings can be useful in imaging distribution of ROS in tissue of a human or mammal, such as, for example, imaging distribution of ROS in the brain of a human or mammal. Imaging distribution of ROS in the brain can be useful, for example, for better understanding the role of ROS in the pathogenesis of Alzheimer's disease, cerebral vascular disease, Parkinson's disease and schizophrenia and for developing therapies as well as monitoring response to therapy. Thus, the present radiotracers and methods can be used, for example, by a medical professional to determine if a therapy is effective.

In some embodiments, a compound of the present teachings can be a radiolabeled compound or salt thereof of structure

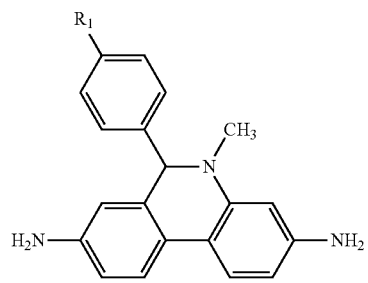

wherein $R_1$ is H or O—$R_3$, $R_3$ is $(CH_2)_q$—$CH_3$,

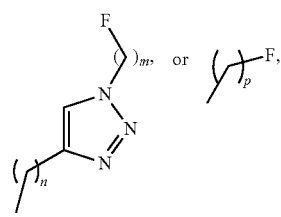

q is an integer from 0 to 10, n is an integer from 0 to 3, m is an integer from 0 to 3, and p is integer from 0 to 3.

In additional embodiments of the present teachings, the inventors disclose methods of imaging ROS distribution in a mammal such as a human. These methods comprise administering to the mammal a radiolabeled compound or salt thereof of structure

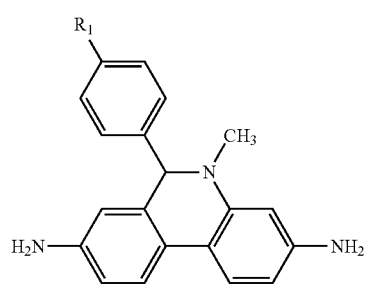

wherein $R_1$ is H or O—$R_3$, $R_3$ is $(CH_2)_q CH_3$,

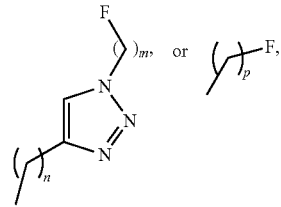

q is an integer from 0 to 10, n is an integer from 0 to 3, m is an integer from 0 to 3, and p is integer from 0 to 3, and subjecting the mammal to PET scanning.

In some embodiments, a compound of the present teachings can be a radiolabeled compound or salt thereof as disclosed herein, wherein $R_1$ is H.

In some embodiments, a compound of the present teachings can be a radiolabeled compound or salt thereof as disclosed herein, wherein $R_1$ is H and the $CH_3$ is $^{11}CH_3$ In some embodiments, a compound of the present teachings can be a radiolabeled compound or salt thereof as disclosed herein, wherein $R_1$ is O—$R_3$, $R_3$ is $(CH_2)_q$—$CH_3$, q is 0.

In some embodiments, a compound of the present teachings can be a radiolabeled compound or salt thereof as disclosed herein, wherein $R_1$ is O—$R_3$, $R_3$ is $CH_3$.

In some embodiments, a compound of the present teachings can be a radiolabeled compound or salt thereof as disclosed herein, wherein $R_1$ is O—$R_3$, $R_3$ is $^{11}CH_3$.

In some embodiments, a compound of the present teachings can be a radiolabeled compound or salt thereof as disclosed herein, wherein $R_1$ is O—$R_3$, wherein $R_3$ is

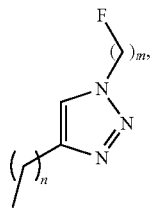

wherein n is an integer from 0 to 3, m is an integer from 0 to 3, and F is $^{18}F$.

In some embodiments, a compound of the present teachings can be a radiolabeled compound of salt thereof as disclosed herein, wherein $R_1$ is O—$R_3$, wherein $R_3$ is

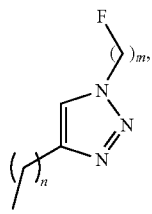

wherein n is 1, m is an integer from 0 to 3, and F is $^{18}F$.

In some embodiments, a compound of the present teachings can be a radiolabeled compound or salt thereof as disclosed herein, wherein $R_1$ is O—$R_3$, wherein $R_3$ is

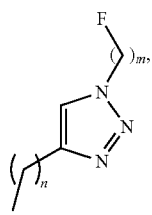

wherein n is an integer from 0 to 3, m is 2, and F is $^{18}F$.

In some embodiments, a compound of the present teachings can be a radiolabeled compound or salt thereof as disclosed herein, wherein $R_1$ is O—$R_3$, wherein $R_3$ is

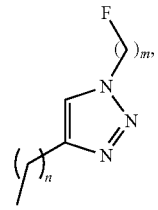

wherein n is 1, m is 2 and F is $^{18}F$.

In some embodiments, a compound of the present teachings can be a radiolabeled compound or salt thereof as disclosed herein, wherein $R_1$ is O—$R_3$, wherein $R_3$ is

wherein p is an integer from 0 to 3 and F is $^{18}F$.

In some embodiments, a compound of the present teachings can be a radiolabeled DHE analogue or salt thereof as disclosed herein, wherein $R_1$ is O—$R_3$, wherein $R_3$ is

wherein p is 2 and F is $^{18}F$.

In various aspects of the above embodiments, a radiolabeled DHE analogue or salt thereof can include particular molecular species, such as

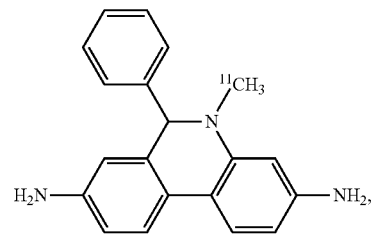

[$^{11}CH_3$]Cl

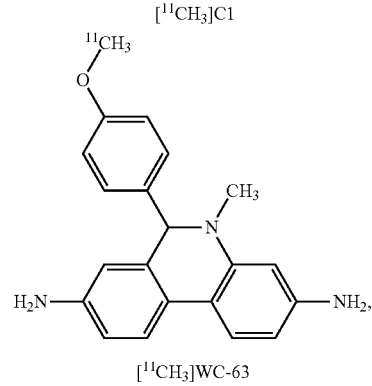

[$^{11}CH_3$]WC-63

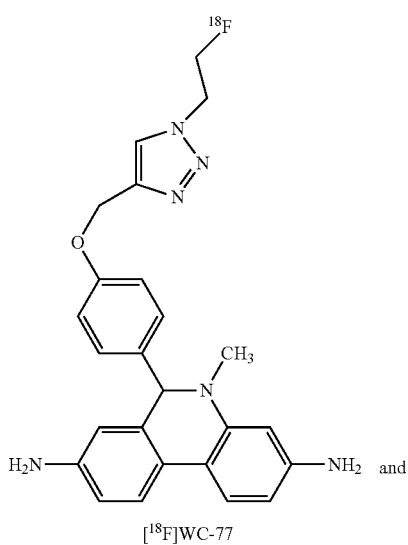

[$^{18}$F]WC-77

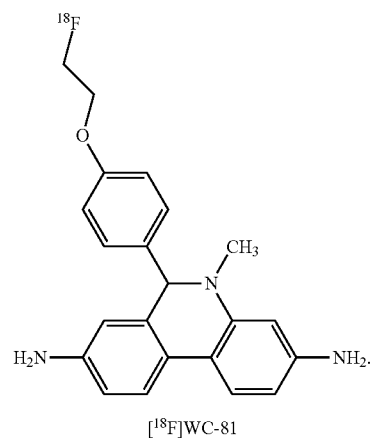

[$^{18}$F]WC-81

In further embodiments of the present teachings, the inventors disclose a radiolabeled compound or salt thereof of structure

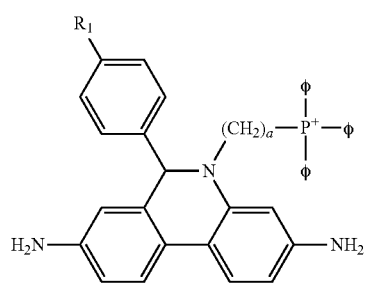

wherein $R_1$ is H or O—$R_3$; $R_3$ is $(CH_2)_q$—$CH_3$,

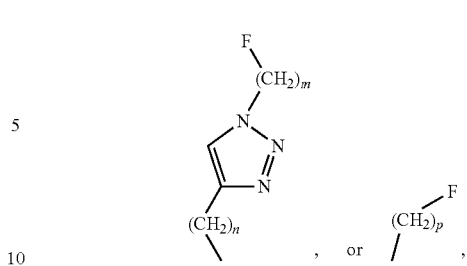

and wherein q is an integer from 0 to 10; n is an integer from 0 to 3; m is an integer from 0 to 3; p is an integer from 0 to 3; and a is an integer from 2 to 10. In some configurations, $R_1$ is H. In some configurations, $CH_3$ is $^{11}CH_3$. φ represents a phenyl group. In some configurations, $R_3$ is $(CH_2)_q$—$CH_3$ and q=0. In some configurations, $R_3$ is $^{11}CH_3$.

In some configurations, $R_3$ is

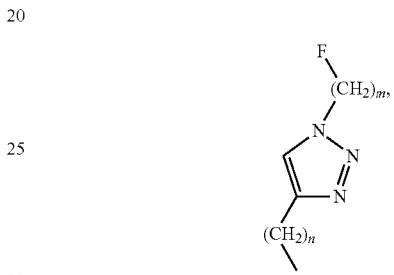

n is an integer from 0 to 3, and m is an integer from 0 to 3. In some configurations, $R_1$ is O—$R_3$, and $R_3$ is $^{11}CH_3$.

In some configurations, the radiolabeled compound or salt thereof is of structure

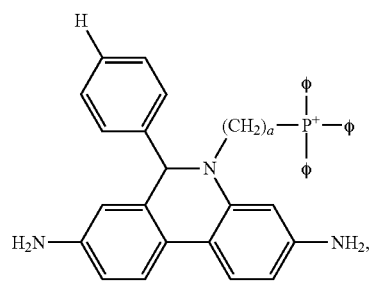

wherein a is an integer from 2 to 10. In some configurations, the radiolabeled compound or salt thereof is of structure

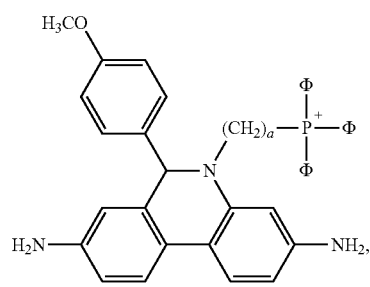

wherein a is an integer from 2 to 10. In some configurations, the radiolabeled compound or salt thereof is of structure

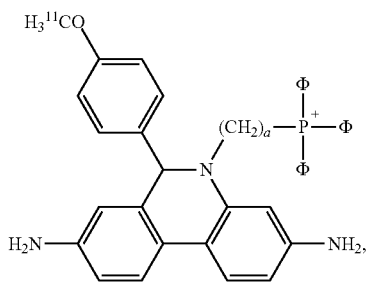

wherein a is an integer from 2 to 10. In some configurations, the radiolabeled compound or salt thereof is of structure

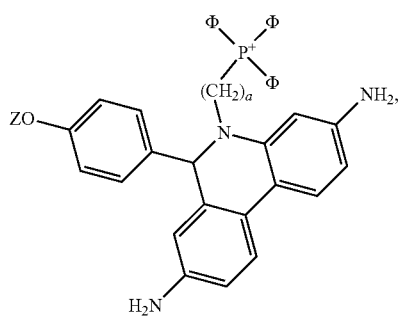

wherein Z is $(CH_2)_q$—$CH_3$, q is an integer from 0 to 10,

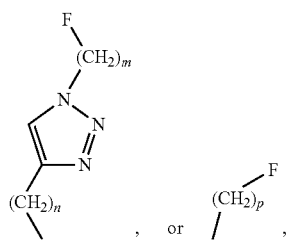

and a is an integer from 2 to 10.

In some configurations, the radiolabeled compound or salt thereof is of structure

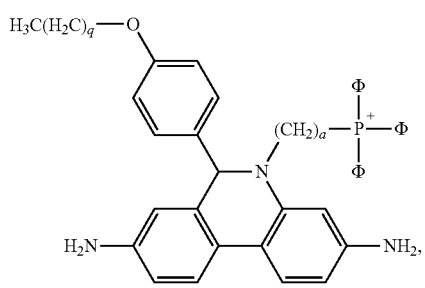

wherein a is an integer from 2 to 10 and q is an integer from 0 to 10. In some configurations, the $CH_3$ can be $^{11}CH_3$. In some configurations, the radiolabeled compound or salt thereof is of structure

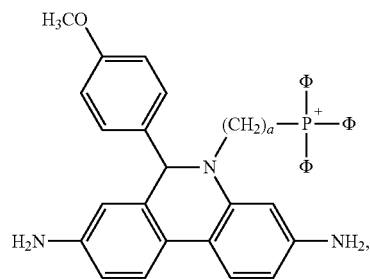

wherein a is an integer from 2 to 10. In some configurations, the radiolabeled compound or salt thereof is of structure

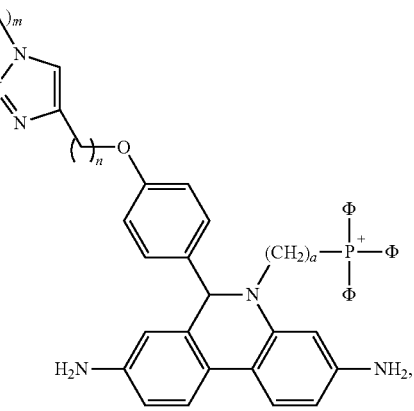

wherein a is an integer from 2 to 10. In some configurations, the radiolableld compound or salt thereof is of structure

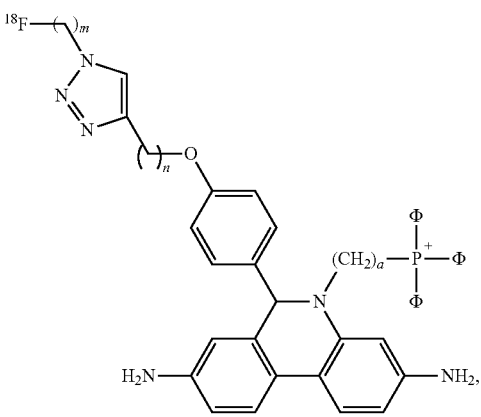

wherein a is an integer from 2 to 10, n is an integer from 0 to 3, and m is an integer from 0 to 3. In some configurations, the radiolabeled compound or salt thereof is of structure wherein a is an integer from 2 to 10, n is an integer from 0 to 3, and m is an integer from 0 to 3. In some configurations, the radiolabeled compound or salt thereof is of structure

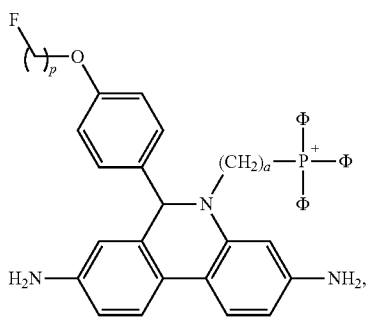

wherein a is an integer from 2 to 10 and p is an integer from 0 to 3. In some configurations the radiolabeled compound or salt thereof is of structure

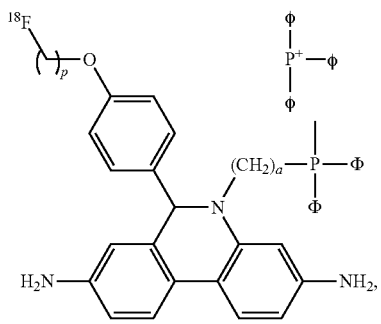

wherein a is an integer from 2 to 10 and p is an integer from 0 to 3.

In various aspects of the embodiments, methods for synthesis of the compounds disclosed herein are provided. In particular aspects, methods of synthesis of radiolabeled compounds or salts thereof are provided. In further aspects, methods for synthesis of radiolabeled DHE analogue precursors are also provided.

EXAMPLES

The following examples are illustrative of the various embodiments of the present teachings. The following examples provide non-limiting illustrations of the present teachings. While some of examples may include conclusions about the way the invention may function, the inventor do not intend to be bound by those conclusions, but put them forth only as possible explanations. Unless noted by use of past tense, presentation of an example does not imply that an experiment or procedure was, or was not, conducted, or that results were, or were not actually obtained. The examples are not intended to limit the scope of any claim.

The methods described herein utilize laboratory techniques well known to skilled artisans, and guidance can be found in laboratory manuals and textbooks such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999; Hedrickson et al., Organic Chemistry 3rd edition, McGraw Hill, New York, 1970; Carruthers, W., and Coldham, I., Modern Methods of Organic Synthesis (4th Edition), Cambridge University Press, Cambridge, U.K., 2004; Curati, W. L., Imaging in Oncology, Cambridge University Press, Cambridge, U.K., 1998; Welch, M. J., and Redvanly, C. S., eds. Handbook of Radiopharmaceuticals: Radiochemistry and Applications, J. Wiley, New York, 2003.

Example 1

This example illustrates synthesis of compound C1, as shown below.

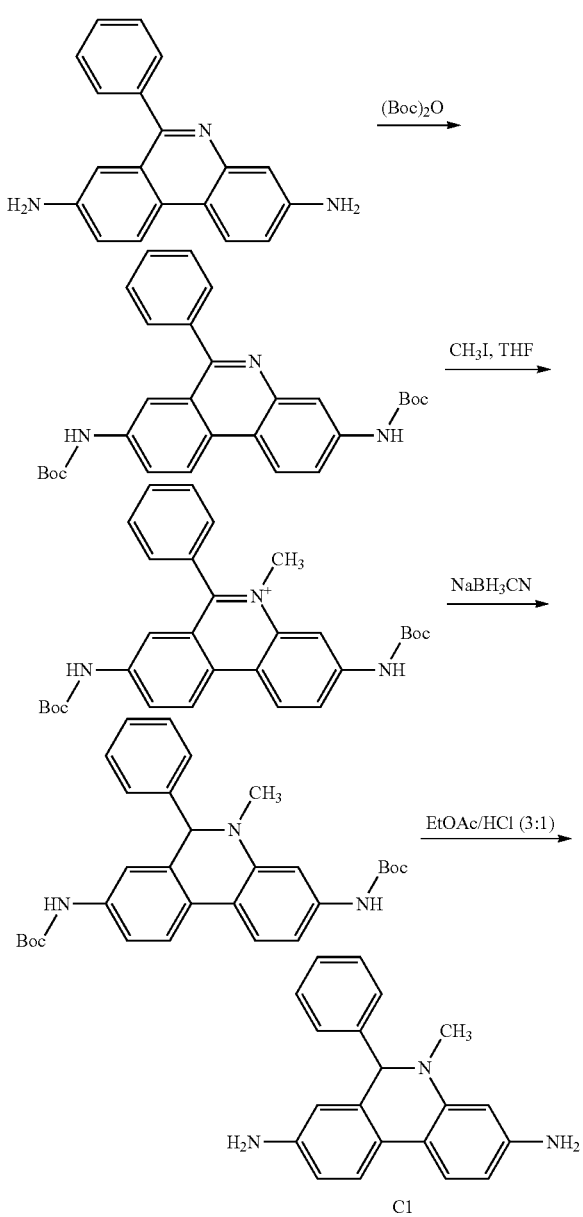

Example 2

This example illustrates synthesis of compound WC-63, as shown below.

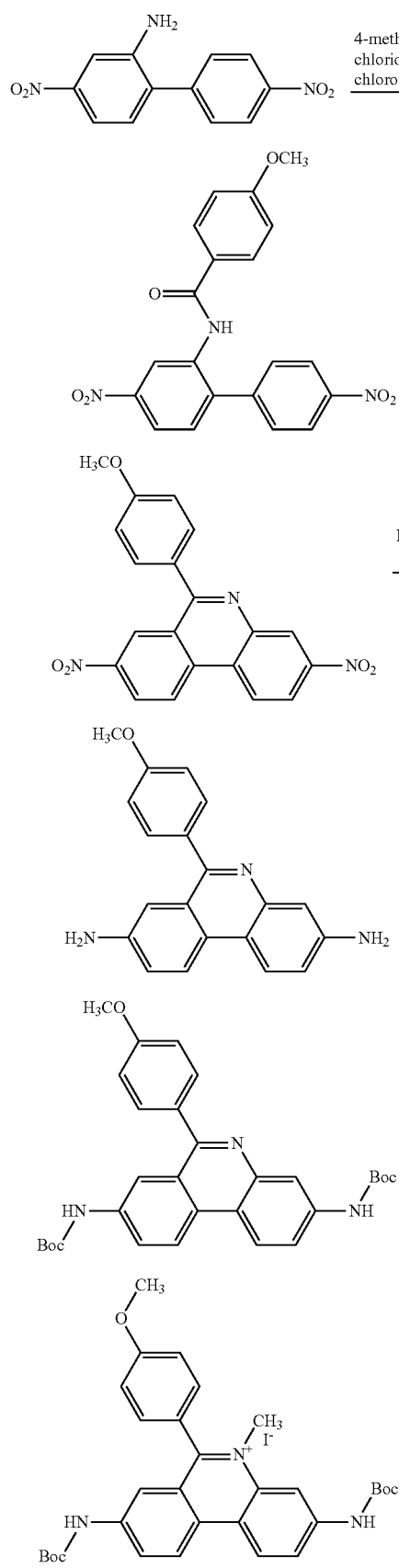
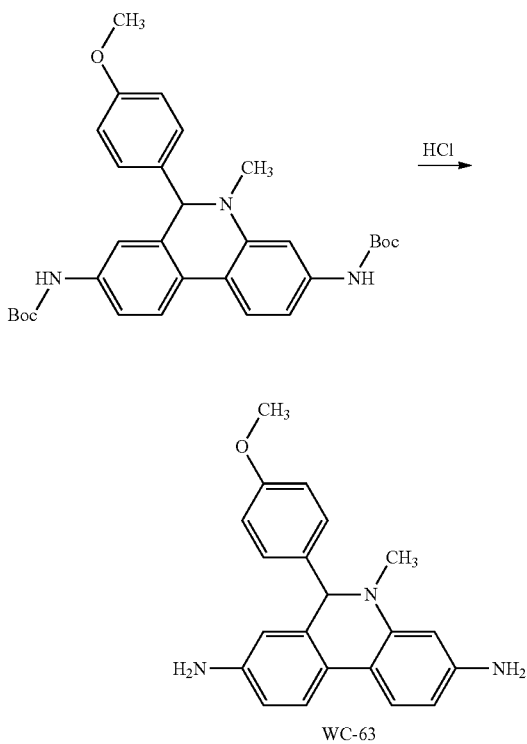
Example 3
This example illustrates synthesis of compound WC-77, as shown below.
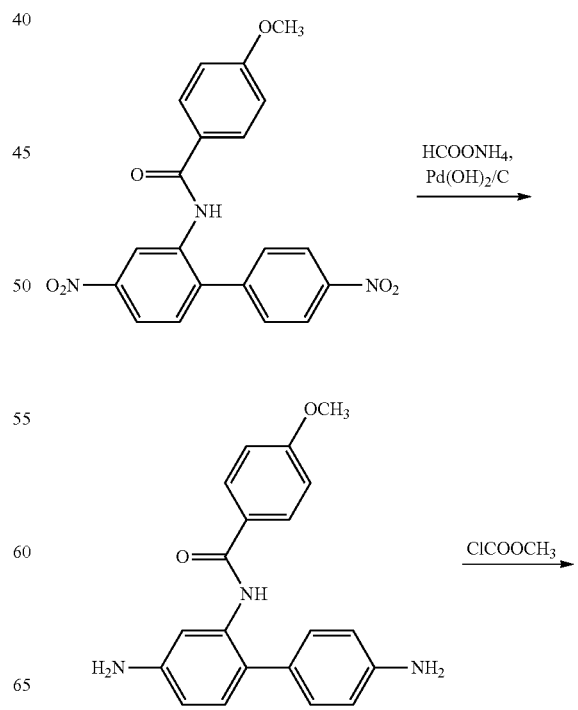

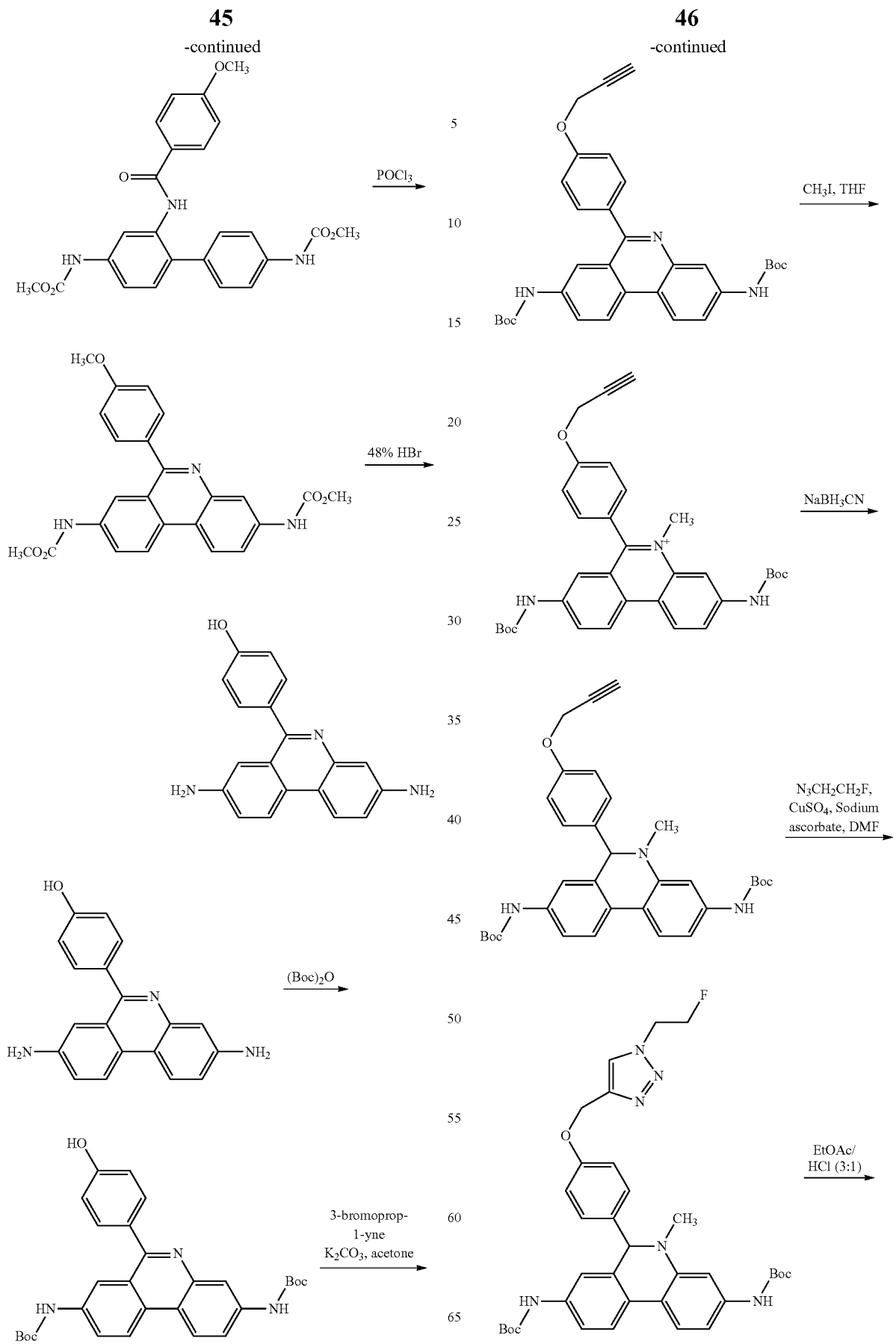

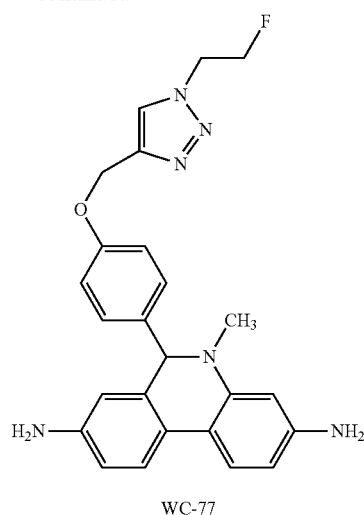
WC-77
Example 4
This example illustrates synthesis of compound WC-81, as shown below.
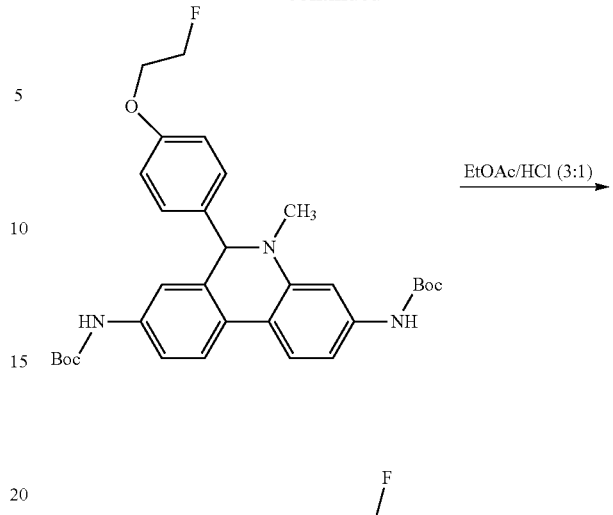
WC-81
Example 5
This example illustrates radiosynthesis of compound [$^{11}CH_3$]C1, as shown below.
Scheme 1:
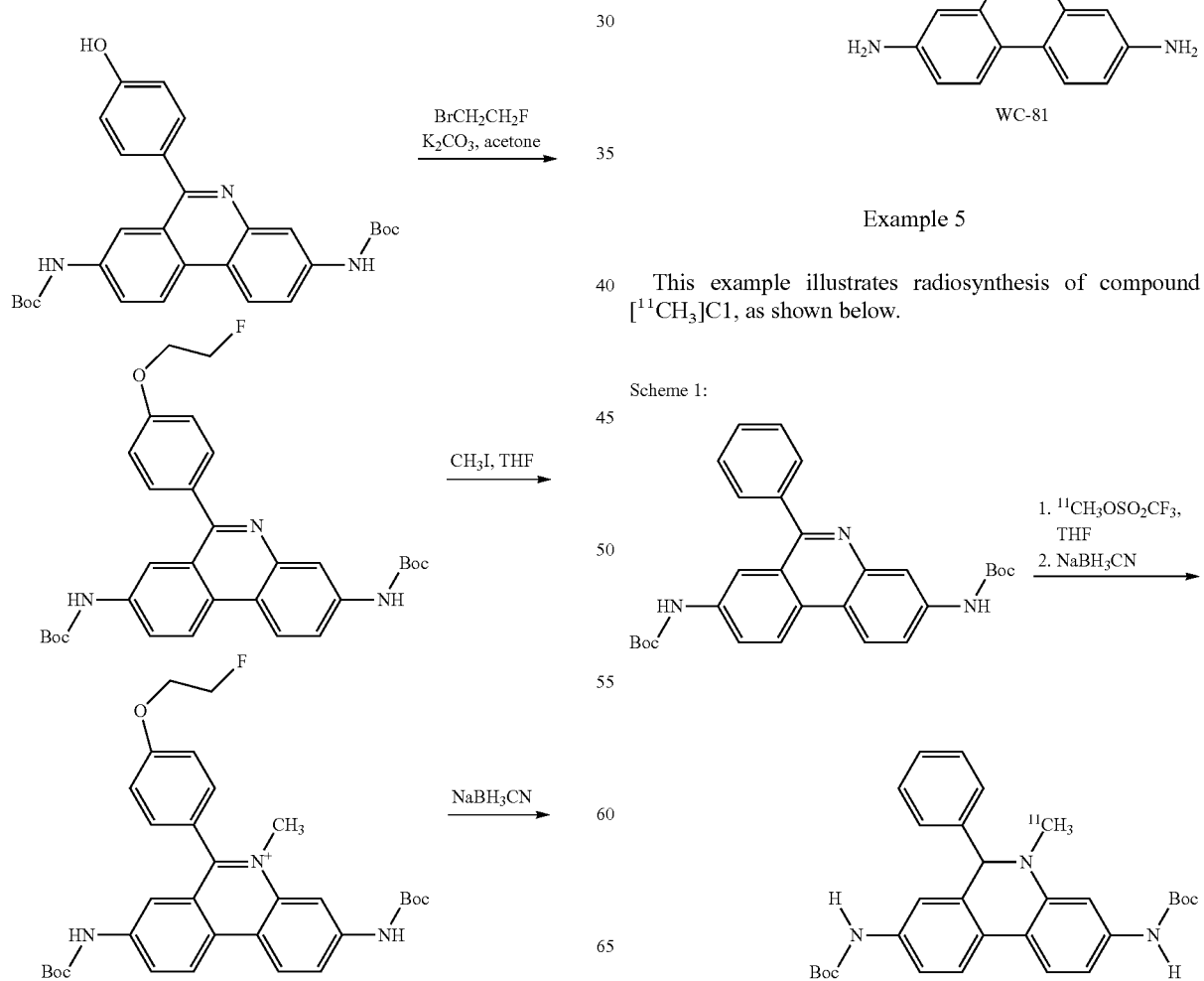

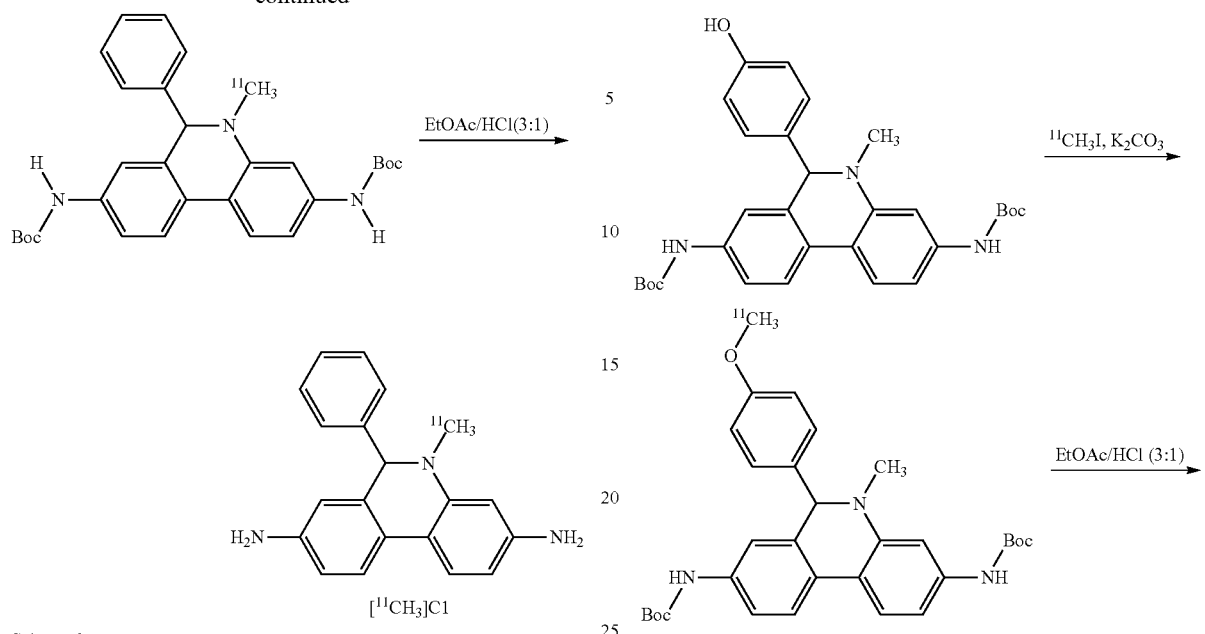

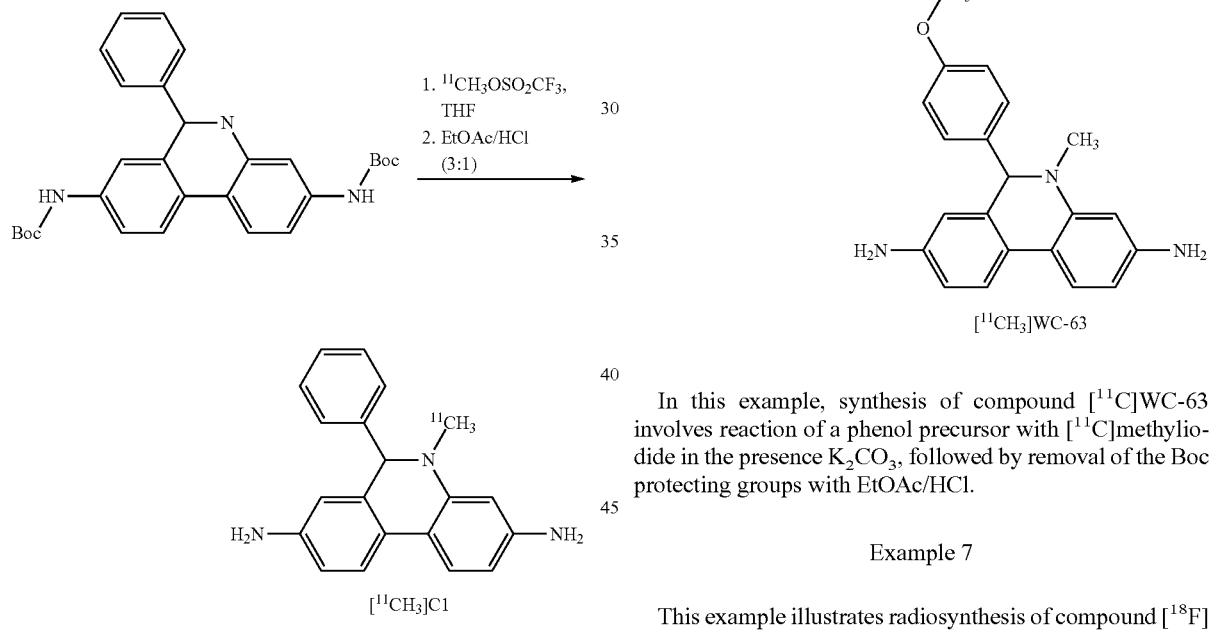

Two different routes for making [¹¹CH₃]C1 are used. The first route (Scheme 1) involves N-alkylation of the phenanthridine analog with [¹¹C]methyltriflate followed by reduction of the nitrogen-carbon double bond with sodium borohydride. Deprotection with HCl results in the formation of [¹¹CH₃]C1. The second approach (Scheme 2) begins with the dihydrophenanthridine analog is then be labeled with [¹¹C] methyltriflate and removal of the butyloxycarbonyl (Boc) protecting goups results in the formation of [¹¹CH₃]C1.

Example 6

This example illustrates a synthesis of radiolabeled compound [¹¹CH₃]WC-63, as shown below.

In this example, synthesis of compound [¹¹C]WC-63 involves reaction of a phenol precursor with [¹¹C]methyliodide in the presence $K_2CO_3$, followed by removal of the Boc protecting groups with EtOAc/HCl.

Example 7

This example illustrates radiosynthesis of compound [¹⁸F] WC-77, as shown below.

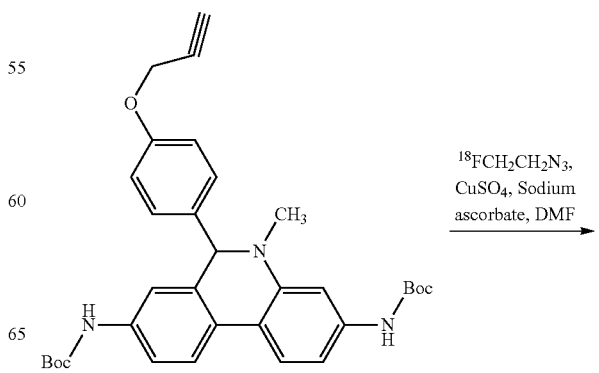

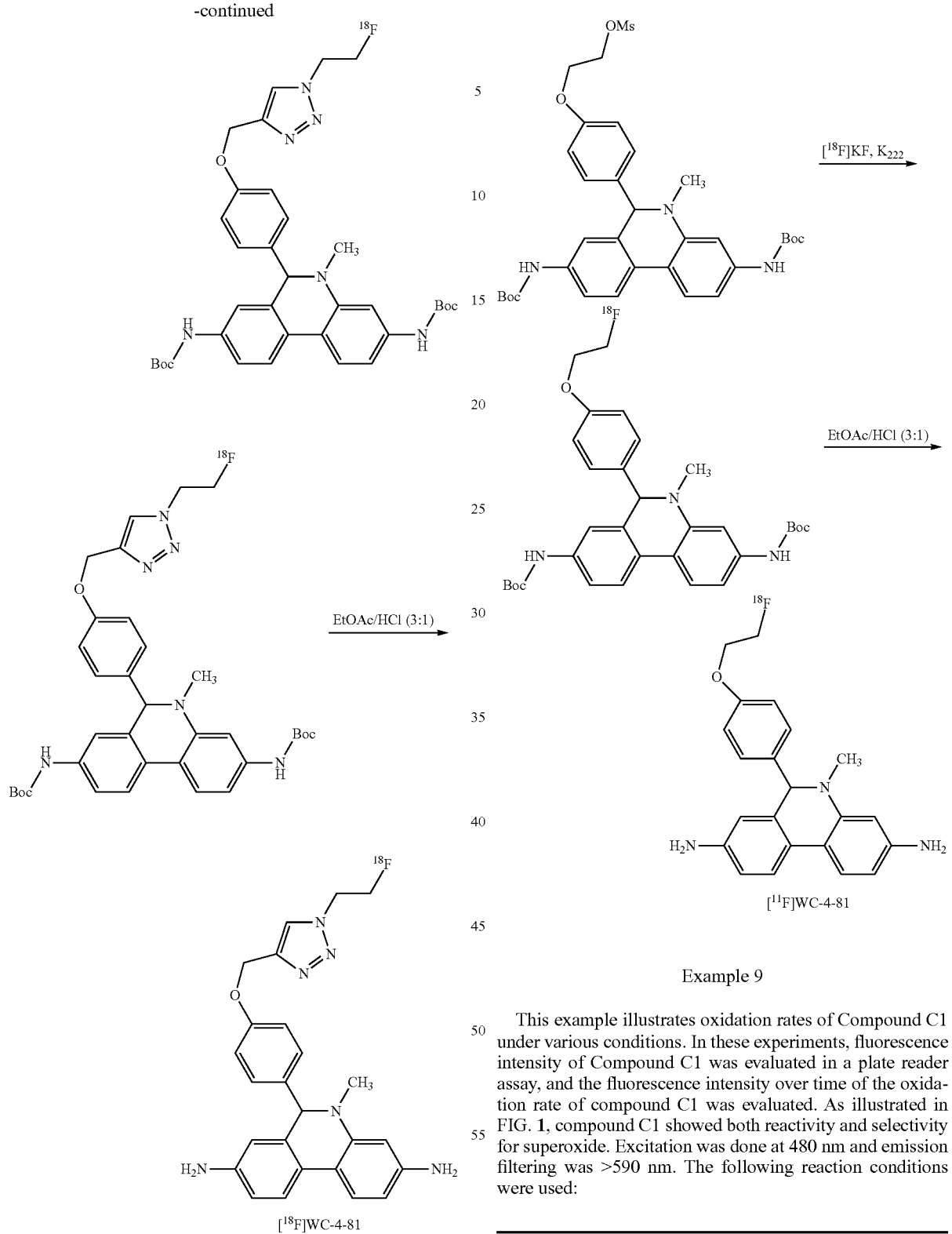

Example 8

This example illustrates radiosynthesis of compound [$^{18}$F] WC-81, as shown below.

Example 9

This example illustrates oxidation rates of Compound C1 under various conditions. In these experiments, fluorescence intensity of Compound C1 was evaluated in a plate reader assay, and the fluorescence intensity over time of the oxidation rate of compound C1 was evaluated. As illustrated in FIG. 1, compound C1 showed both reactivity and selectivity for superoxide. Excitation was done at 480 nm and emission filtering was >590 nm. The following reaction conditions were used:

| | |
|---|---|
| C1 | 158 μM |
| XO | 0.052 U/ml |
| hypoxanthine | 1 mM |
| SOD | 575 U/ml |
| Catalase | 60 U/ml |
| Hydrogen peroxide | 1 mM |
| HRP | 0.2 U/ml |

Under the conditions of superoxide production with hypoxanthine and xanthine oxidase (XO system), compound C1 is oxidized rapidly. Compound C1 showed no oxidation with peroxide ($H_2O_2$), or $H_2O_2$ with horseradish peroxidase. Superoxide dismutase (SOD), which rapidly removes superoxide, also completely removed compound C1 oxidation. Finally, addition of catalase, which removes $H_2O_2$, did not effect compound C1 oxidation, demonstrating independence from $H_2O_2$. The rate of conversion by oxidation of C1 was slightly faster than DHE itself (data not shown) and was selective for superoxide as there was no observable oxidation from $H_2O_2$ or $H_2O_2$ in the presence of horseradish peroxidase (to generate the hydroxyl radical, HO—).

Example 10

Figure 2:
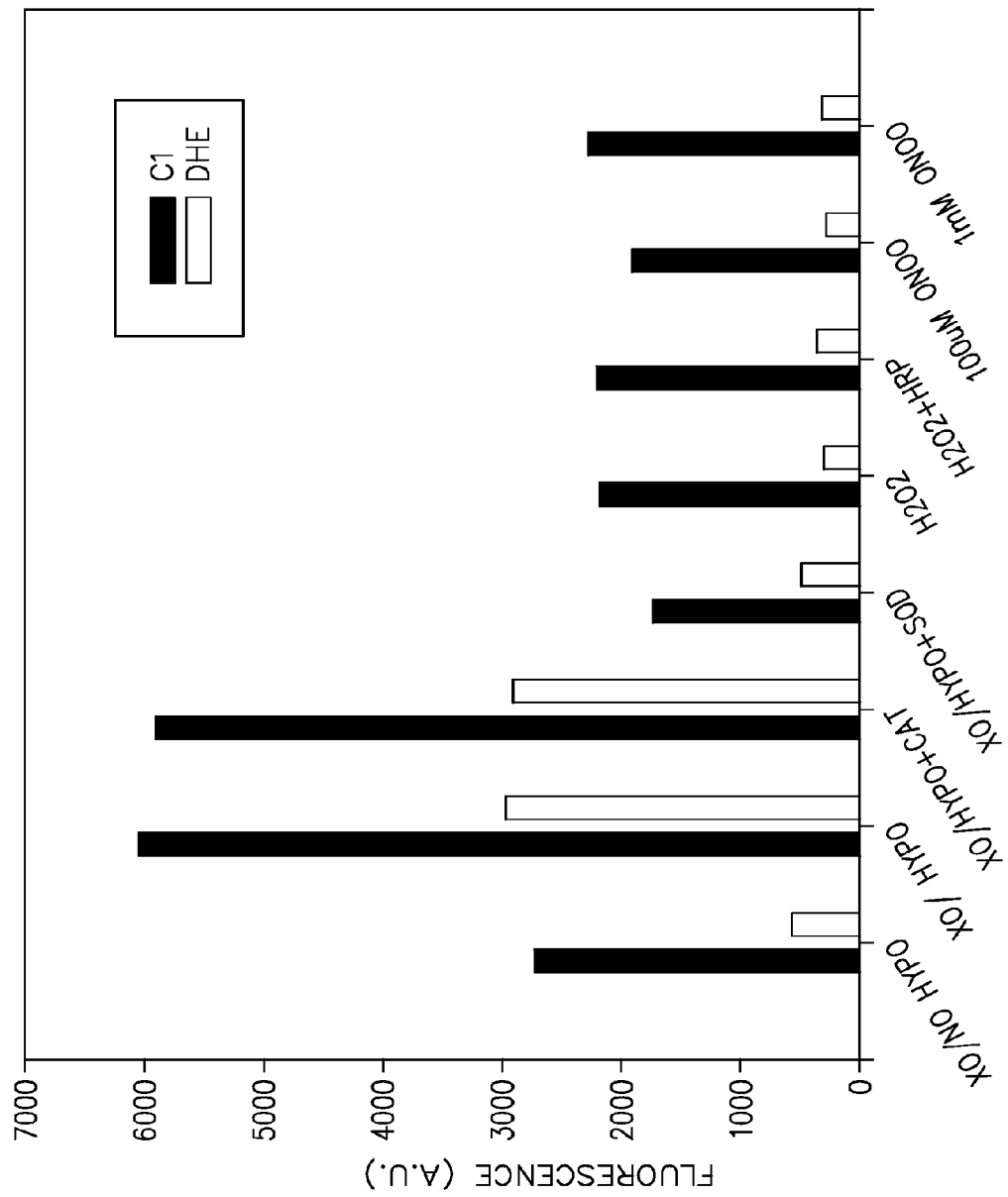
FIG. 2 presents the production of C1 oxidation fluorescence signal compared to DHE for a variety of conditions.

This example illustrates comparative oxidation of C1 and DHE. In these experiments, fluorescence of C1 or DHE were determined in the presence of oxidizers. As shown in FIG. 2, C1 showed selective oxidation similar to DHE with elevations in the presence of superoxide but not in the presence of peroxide ($H_2O_2$), hydroxyl radical (HO—) or peroxynitrate (ONOO—). In this single wavelength fluorescence platereader study, it should be noted that the ratio of fluorescence increase in a study cannot be compared between DHE and compound C1 since their non-oxidized forms have fluorescence and the light spectra overlap to a variable degree with the oxidized forms.

Example 11

Figure 3:
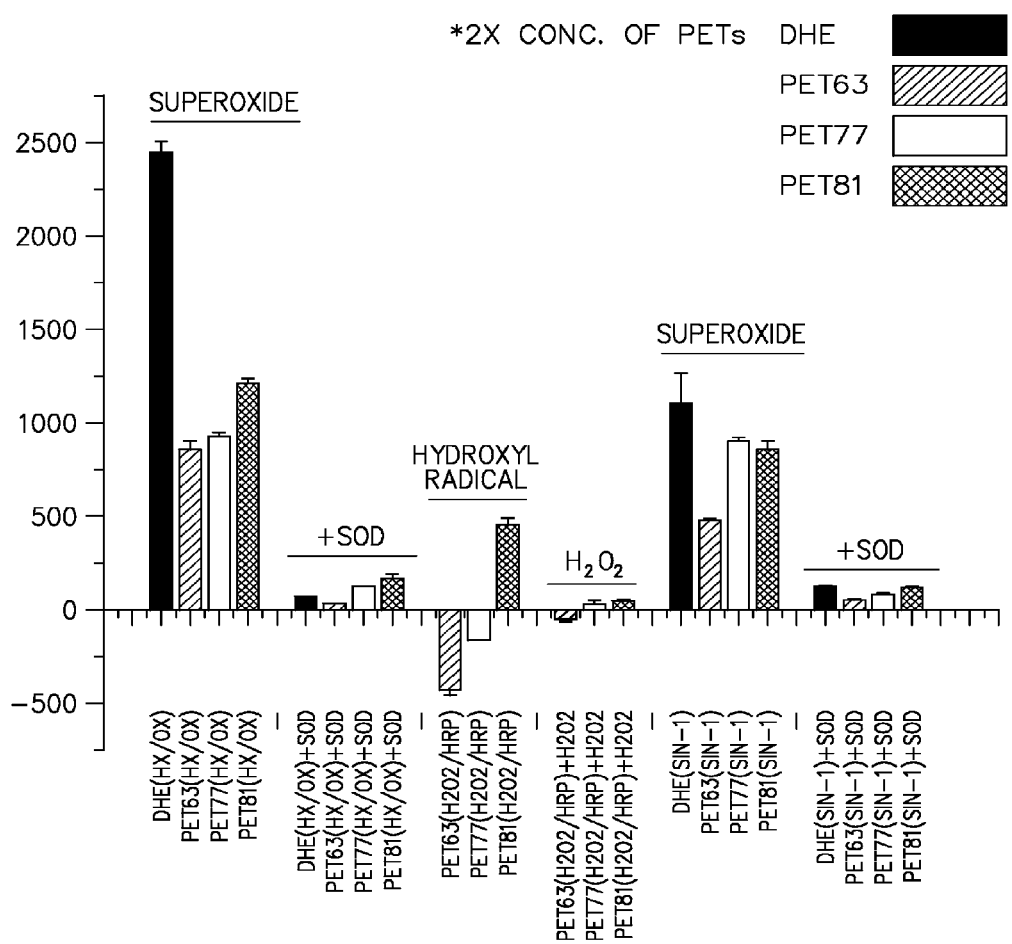
FIG. 3 presents a comparison of compounds WC-63, WC-77 and WC-81 for selective reactivity with superoxide radical.
Figure 4A:
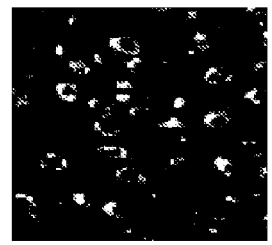
FIG. 4 presents confocal microscope images of in vivo oxidation of compound C1 in mouse brains pretreated with subanesthetic doses of ketamine and sacrificed 16 hours after administration of compound C1.
Figure 4B:
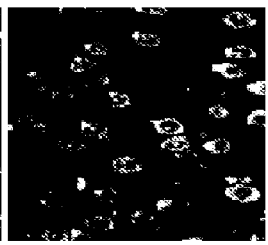
Figure 4C:
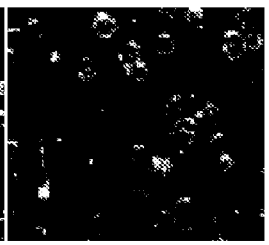
Figure 4D:
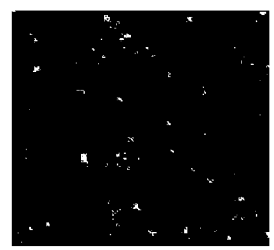
Figure 4E:
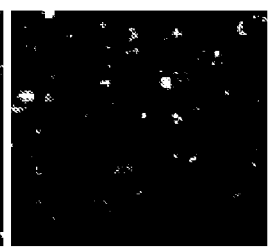
Figure 4F:
Figure 4G:
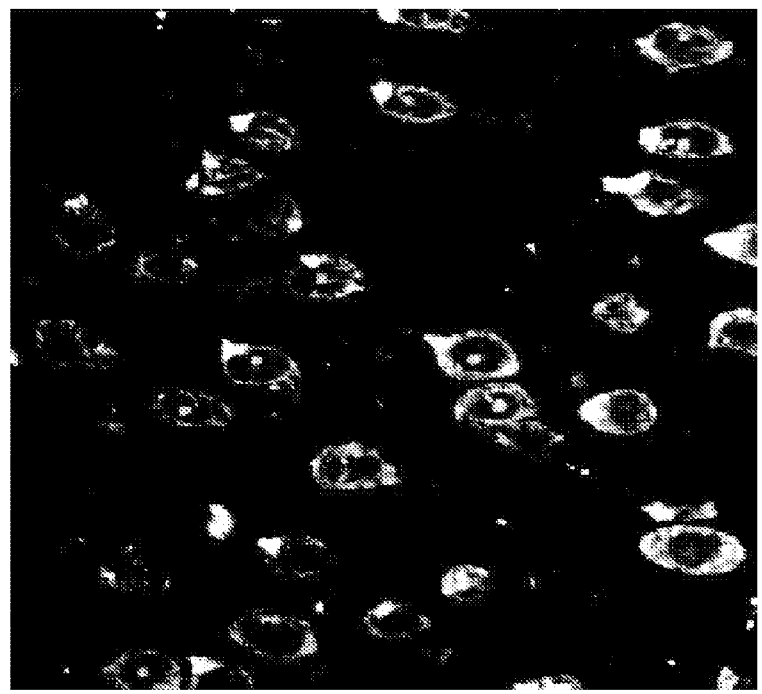

This example illustrates a comparison of compounds for selective reactivity with superoxide radical. In these experiments, compounds WC-63, WC-77 and WC-81 were exposed to superoxide generated by xanthine oxidase/hypoxanthine in the absence or presence SOD, and were evaluated similarly as compound C1 in Example 10. The concentration of DHE for all experiments was double that of compounds WC-63, WC-77 and WC-81. As shown in FIG. 3, compounds WC-63, WC-77 and WC-81 showed high specificity for superoxide with generally no evidence of oxidation with $H_2O_2$ or hydroxyl radical. The exception was compound WC-81, which had partial oxidation in the presence of the hydroxyl radical at these supraphysiologic levels, but remained intact Change in fluorescent units from baseline is shown on the y-axis under same conditions as FIG. 2. The data showed that DHE, WC-63, WC-77 and WC-81 were each oxidized by superoxide, and that SOD fully blocked oxidation, indicating that oxidation is superoxide-dependent. All of the compounds were also exposed to $H_2O_2$ in the presence of horseradish peroxidase (HRP) to generate hydroxyl radical. $H_2O_2$ alone did not oxidize any of the compounds. A second method of generating superoxide through SIN-1 decomposition (Sydnonimine-1, an extracellular donor of NO and superoxide, Panagiotidis, G., et al., Br. J. Pharmacol. 114: 289-296, 1995) also indicated that all 4 compounds detect superoxide, and SOD was able to block oxidation completely. Compound WC-77 was the most specific compound for superoxide, but compound WC-81 was the most stable and intact product. It was still highly selective for superoxide under our experimental conditions, in which the levels of hydroxyl radical were very supraphysiological.

Example 12

This example illustrates imaging of oxidation of Compound C1 in an animal model.

Figure 5:
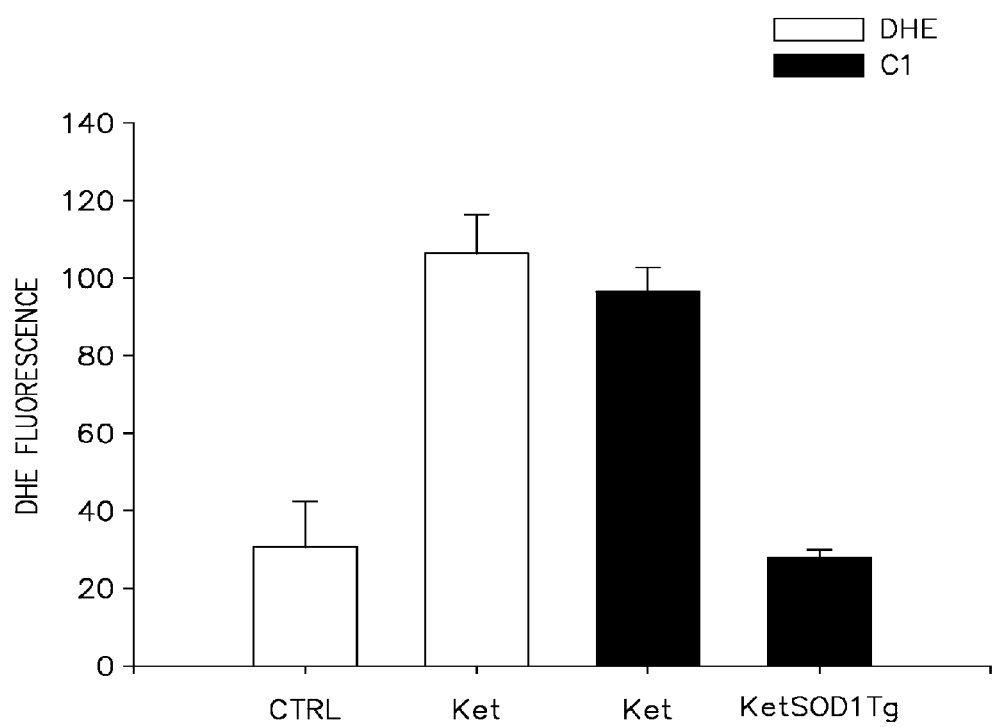
FIG. 5 presents quantitative measures of fluorescence of oxidized forms of DHE and compound C1 in mouse brain.

In these experiments, mice were pretreated for several days with subanesthetic doses of ketamine, which produces a large increase in neuronal superoxide generation (Behrens et al, 2007). The mice were injected with 27 mg/kg of compound C1 and sacrificed 16 hours later. Brains were sliced and imaged by confocal microscopy. The images of the brains sliced 16 hours after administration of compound C1 are depicted in FIG. 4. The images show a pattern of fluorescence consistent with the presence of intracellular oxidized compound C1. As shown in FIG. 5, both DHE and compound C1 detected a large increase in superoxide produced by ketamine treatment. The quantitative measures of fluorescence of the oxidized forms of DHE and compound C1 in mouse brain are depicted in FIG. 5. When compound C1 was administered to transgenic mice overexpressing SOD, the increased fluorescence from the ketamine pretreatment was abolished, consistent with the SOD removal of superoxide (FIG. 5).

Example 13

This example illustrates kinetics of Compound WC-81 in brain in vivo.

Figure 6:
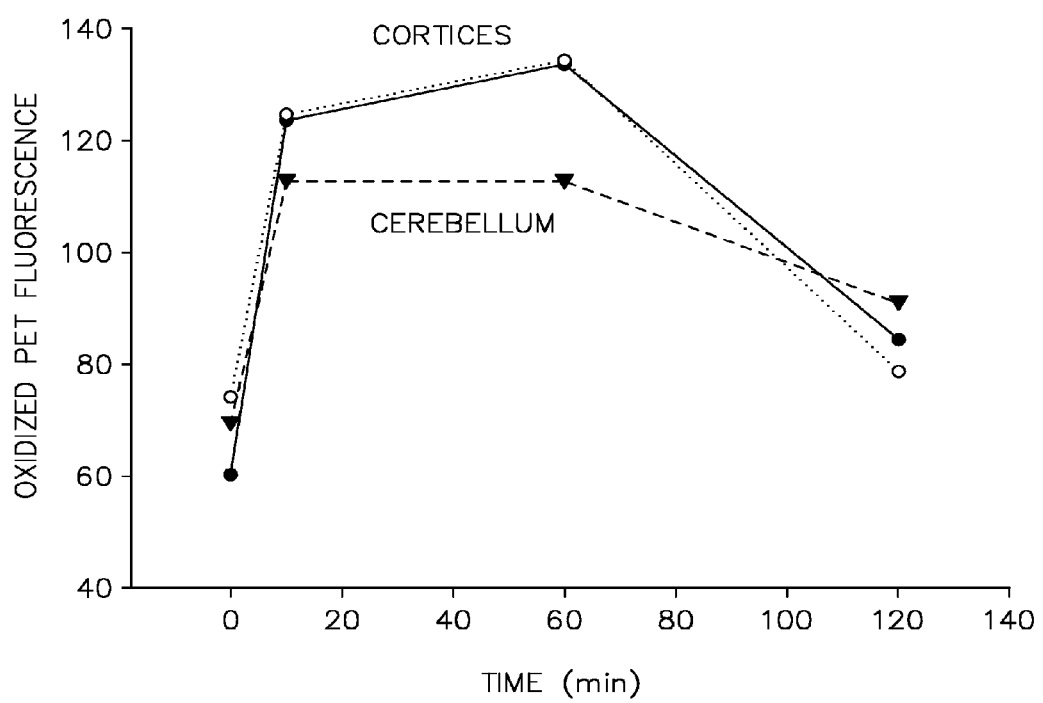
FIG. 6 presents quantitative measures of regional brain fluorescence of compound WC-81 in the cortices and cerebellum of live mice.

In these experiments, an anesthetized mouse was placed in an eXplore Optix™-MX2 scanner, and an initial scan was completed for background fluorescence (T=0). A single intraperitoneal injection of 50 mg/kg of compound WC-81 in 50% DMSO, 50% saline was performed, and the animal was rescanned at 10 minutes. It took approximately 5 minutes to complete the scan. The mouse was removed, allowed to recover, then re-anesthetized and rescanned at 1 hour. A similar recovery and rescan was performed at 2 hours. The mouse was pretreated with subanesthetic doses of ketamine to raise superoxide levels. Cortical (left and right) and cerebellar activity are depicted in FIG. 6. The results show that compound WC-81 penetrated the brain. While a plateau was reached by 60 minutes, there was a fall in levels at 120 minutes.

Example 14

Figure 7A:
FIG. 7 presents images of oxidation of compound WC-81 in mouse brain. Panel. A shows oxidation of compound WC-81 localized in the extracellular space around cortical neurons. Panel B shows oxidation of compound WC-81 localized in the extracellular space around hippocampal neurons. Panel C shows oxidation of compound WC-81 localized in cerebral microvessels.
Figure 7B:
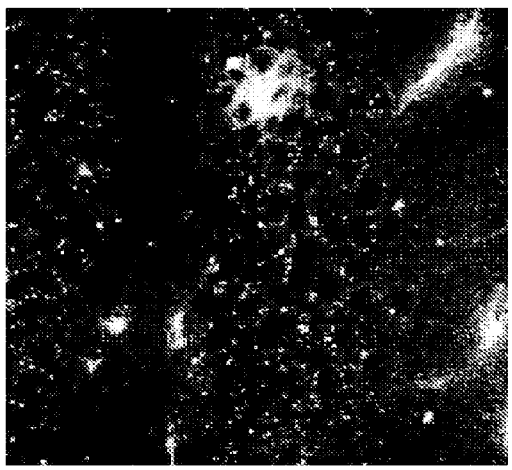
Figure 7C:
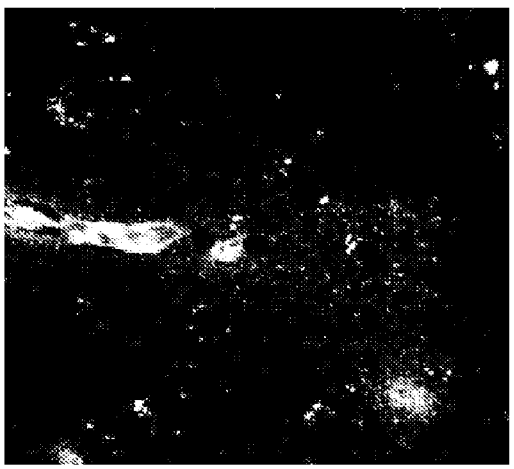
Figure 8A:
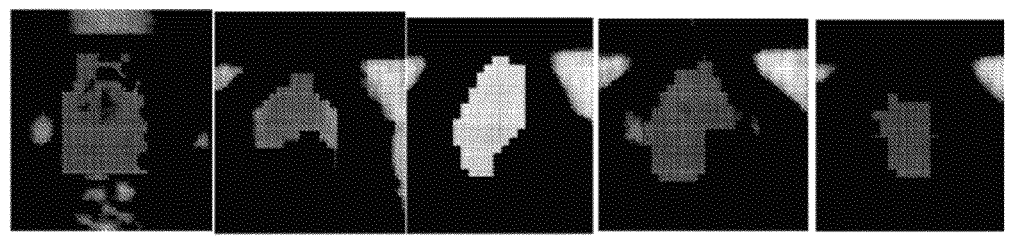
FIG. 8A-D presents images of fluorescence lifetimes for the oxidation products of compounds WC-63, WC-77 and WC-81 in the brain and chest.
Figure 8A:
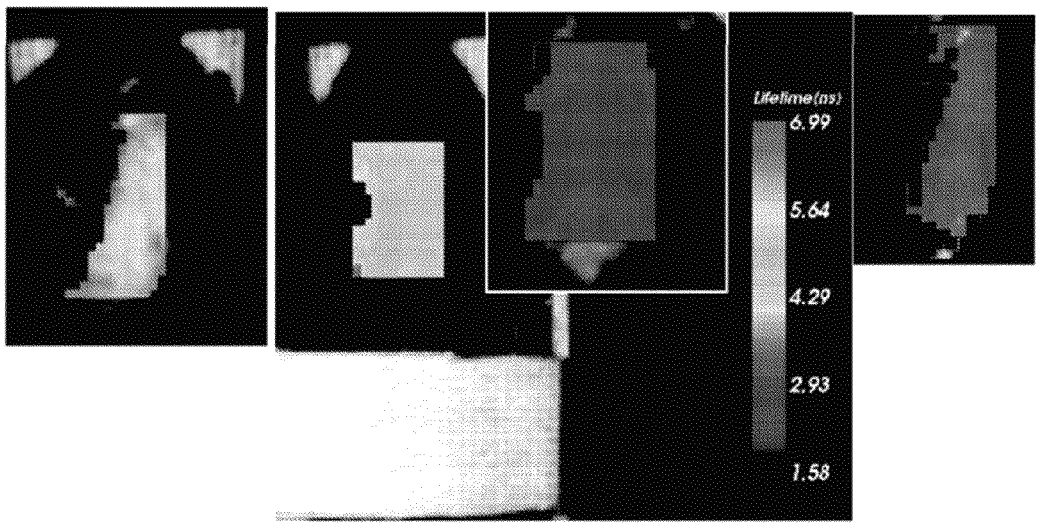
Figure 8B:
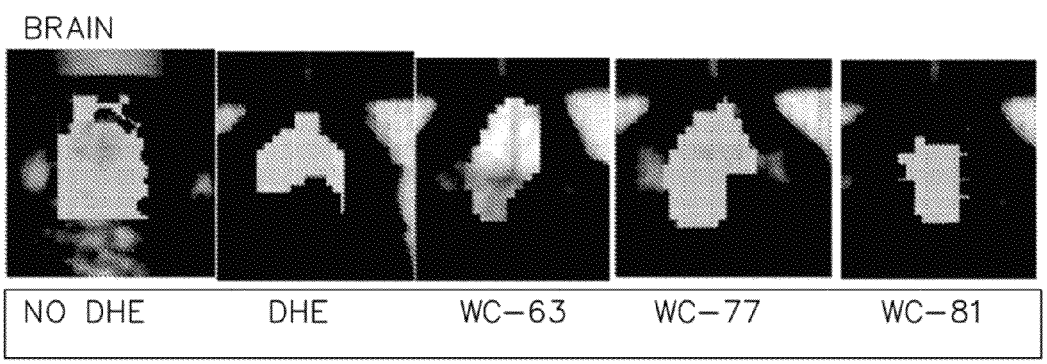
Figure 8B:
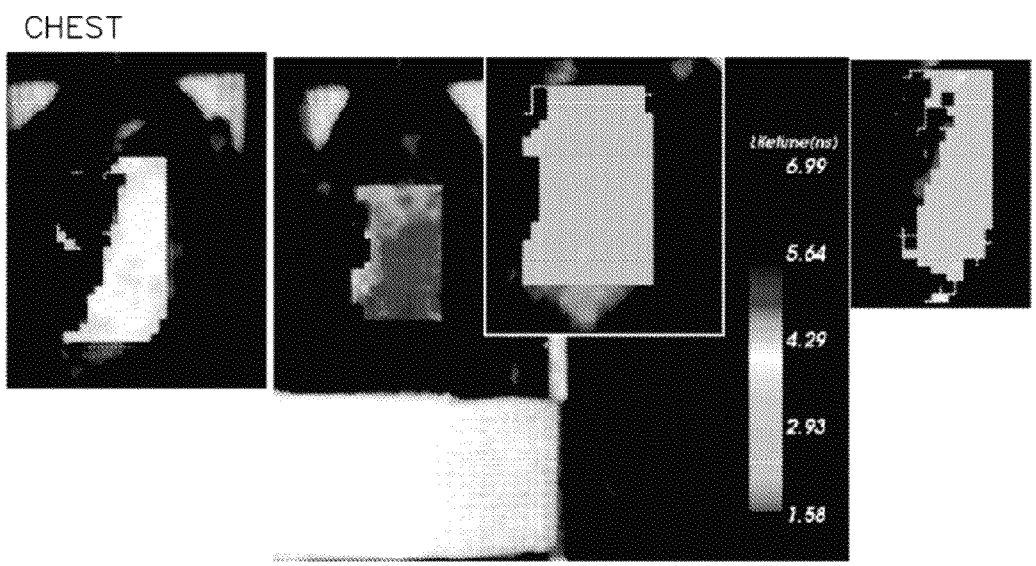
Figure 8C:
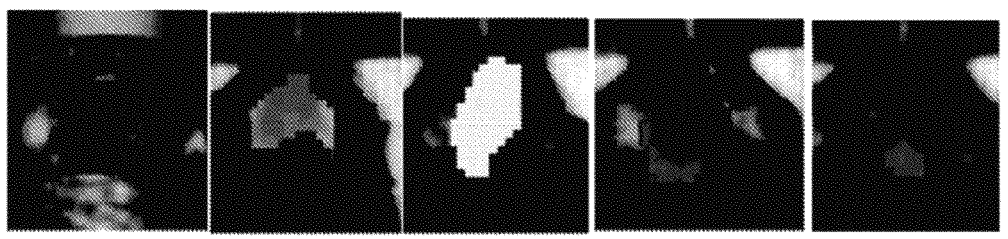
Figure 8C:
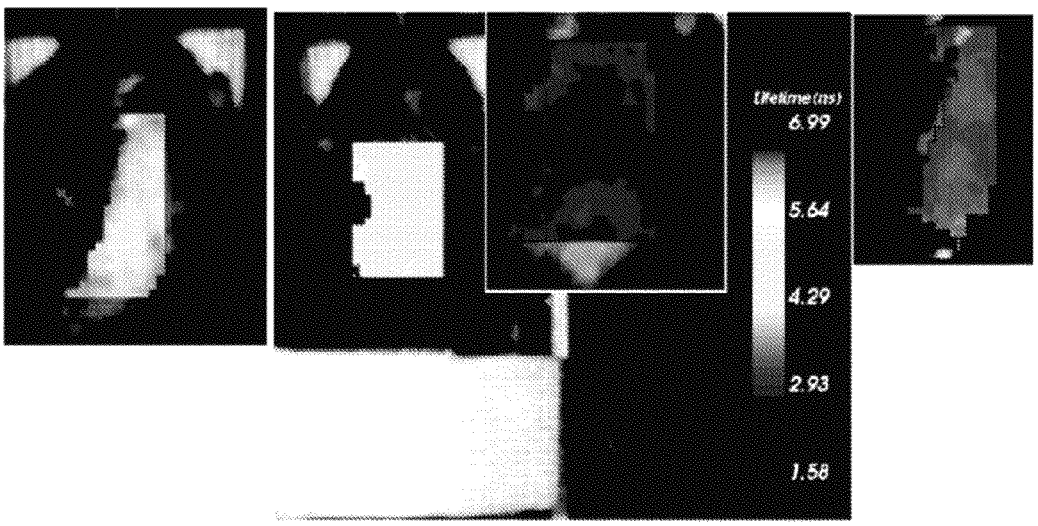
Figure 8D:
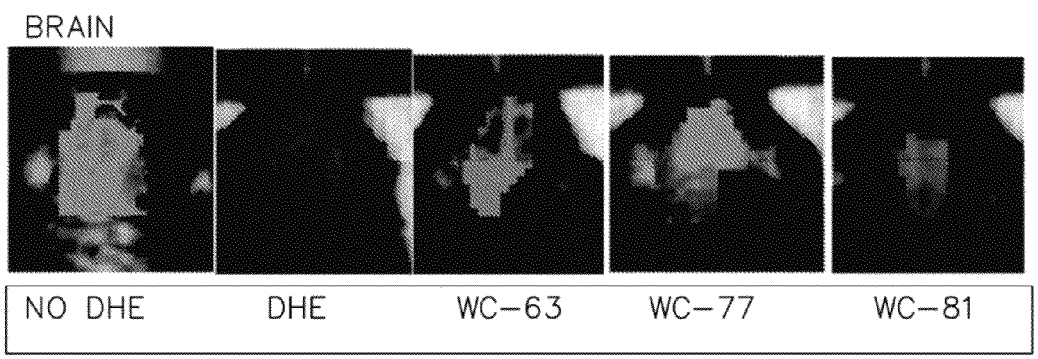
Figure 8D:
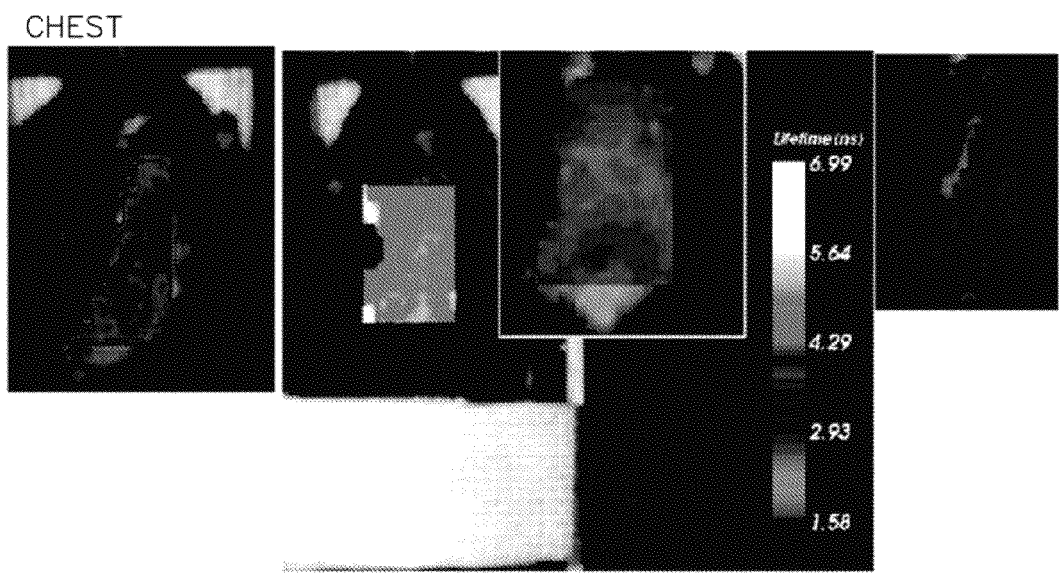

This example illustrates fluorescence from oxidation of Compound WC-81. In these experiments, compound WC-81 was administered to mice, and images of mouse brains were then obtained (FIG. 7). Fluorescence from oxidation of compound WC-81 was localized to cerebral microvessels and to the extracellular space around certain cortical or hippocampal neurons.

Example 15

This example illustrates tissue uptake of the tracers. In these experiments, tracer lifetimes in mice were studied by fluorescence imaging of DHE and compounds WC-63, WC-77 and WC-81. As shown in FIG. 8, DHE, compounds WC-63 and WC-81 are present in the brain and organs in the chest.

All references cited herein are incorporated by reference, each in its entirety.

What is claimed is:

1. A radiolabeled compound or salt thereof of structure

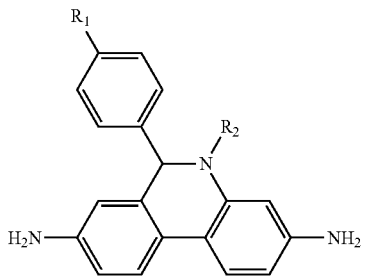

wherein $R_1$ is H or O—$R_3$, $R_3$ is $(CH_2)_q CH_3$,

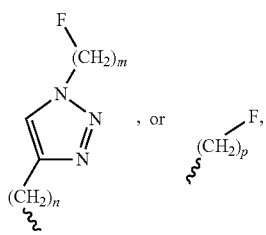, or 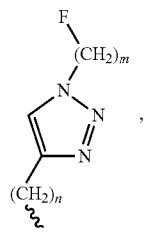

q is an integer from 0 to 10; n is an integer from 0 to 3, m is an integer from 0 to 3, p is an integer from 0 to 3, $R_2$ is methyl or

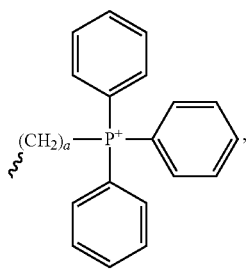

a is an integer from 0 to 10, wherein at least one atom is a radioisotope and ⌇ is a bond.

2. A radiolabeled compound or salt thereof in accordance with claim 1, wherein the radioisotope is a positron-emitting radioisotope.

3. A radiolabeled compound or salt thereof in accordance with claim 1 wherein $R_1$ is H.

4. A radiolabeled compound or salt thereof in accordance with claim 1, wherein the compound or salt thereof comprises an $^{11}CH_3$.

5. A radiolabeled compound or salt thereof in accordance with claim 1, wherein $R_3$ is $(CH_2)_q$—$CH_3$ and q is 0.

6. A radiolabeled compound or salt thereof in accordance with claim 5, wherein $R_3$ is $^{11}CH_3$.

7. A radiolabeled compound or salt thereof in accordance with claim 1, wherein $R_3$ is

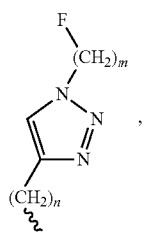

n is an integer from 0 to 3, m is an integer from 0 to 3 and ⌇ is a bond.

8. A radiolabeled compound or salt thereof in accordance with claim 1, wherein $R_1$ is O—$R_3$, $R_3$ is $CH_3$.

9. A radiolabeled compound or salt thereof in accordance with claim 8, wherein $R_1$ is O—$R_3$, wherein $R_3$ is $^{11}CH_3$.

10. A radiolabeled compound or salt thereof in accordance with claim 1, wherein $R_1$ is O—$R_3$, $R_3$ is n is an integer from 0 to 3, m is an integer from 0 to 3, F is $^{18}F$ and ⌇ is a bond.

11. A radiolabeled compound or salt thereof in accordance with claim 10, wherein n is 1.

12. A radiolabeled compound or salt thereof in accordance with claim 10, wherein m is 2.

13. A radiolabeled compound or salt thereof in accordance with claim 10, wherein n is 1 and m is 2.

14. A radiolabeled compound or salt thereof in accordance with claim 1, wherein $R_3$ is,

p is an integer from 0 to 3, F is $^{18}F$ and ⌇ is a bond.

15. A radiolabeled compound or salt thereof in accordance with claim 13, wherein p is 2.

16. A radiolabeled compound or salt thereof in accordance with claim 1, wherein the compound is selected from the group consisting of

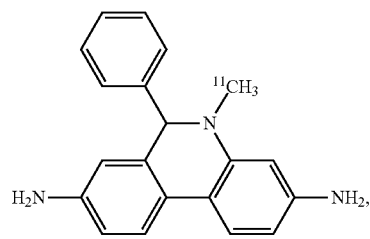

[$^{11}CH_3$]Cl

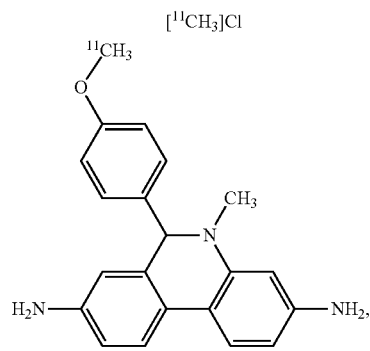

[$^{11}CH_3$]WC-63

-continued
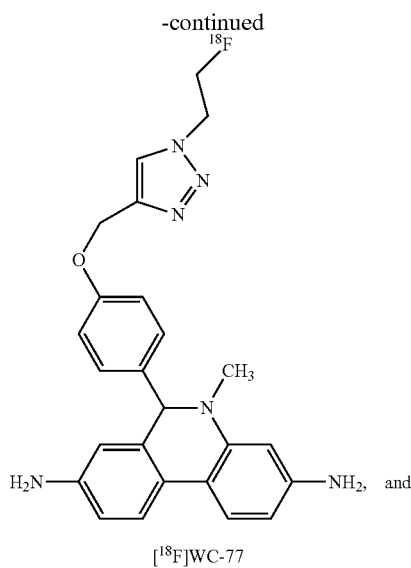
[18F]WC-77, and
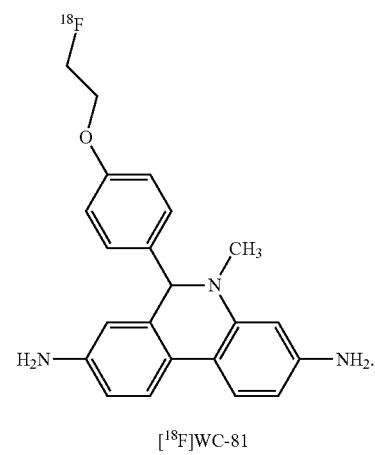
[18F]WC-81.
* * * * *